(12) United States Patent
Bridon et al.

(10) Patent No.: US 8,039,432 B2
(45) Date of Patent: Oct. 18, 2011

(54) METHOD OF TREATMENT OF DIABETES AND/OR OBESITY WITH REDUCED NAUSEA SIDE EFFECT

(75) Inventors: Dominique P. Bridon, San Francisco, CA (US); Jean-Paul Castaigne, Mont-Royal (CA); Karen Thibaudeau, Rosemere (CA)

(73) Assignee: Conjuchem, LLC, Culver City, CA (US)

( * ) Notice: Subject to any disclaimer, the term of this patent is extended or adjusted under 35 U.S.C. 154(b) by 109 days.

(21) Appl. No.: 11/595,576

(22) Filed: Nov. 9, 2006

(65) Prior Publication Data

US 2007/0207958 A1   Sep. 6, 2007

Related U.S. Application Data

(60) Provisional application No. 60/735,404, filed on Nov. 9, 2005.

(51) Int. Cl.
*A61K 38/26* (2006.01)
*A61K 38/28* (2006.01)
*A61K 38/38* (2006.01)

(52) U.S. Cl. .......... 514/6.7; 514/6.8; 514/6.9; 514/7.2; 514/15.2

(58) Field of Classification Search .............. None
See application file for complete search history.

(56) References Cited

U.S. PATENT DOCUMENTS

| | | | |
|---|---|---|---|
| 4,206,199 A | 6/1980 | Fujino et al. |
| 4,251,631 A | 2/1981 | Simon |
| 4,423,034 A | 12/1983 | Nakagawa et al. |
| 4,462,941 A | 7/1984 | Lee et al. |
| 4,745,100 A | 5/1988 | Gilbard et al. |
| 4,766,106 A | 8/1988 | Katre et al. |
| 4,859,604 A | 8/1989 | Gould et al. |
| 4,902,505 A | 2/1990 | Pardridge et al. |
| 5,103,233 A | 4/1992 | Gallagher et al. |
| 5,118,666 A | 6/1992 | Habener |
| 5,120,712 A | 6/1992 | Habener |
| 5,424,286 A | 6/1995 | Eng |
| 5,493,007 A | 2/1996 | Burnier et al. |
| 5,545,618 A | 8/1996 | Buckley et al. |
| 5,574,008 A | 11/1996 | Johnson et al. |
| 5,580,853 A | 12/1996 | Sytkowski |
| 5,612,034 A | 3/1997 | Pouletty et al. |
| 5,612,458 A | 3/1997 | Hyldig-Nielsen et al. |
| 5,614,487 A | 3/1997 | Battersby et al. |
| 5,614,492 A | 3/1997 | Habener |
| 5,654,276 A | 8/1997 | Barrett et al. |
| 5,705,483 A | 1/1998 | Galloway et al. |
| 5,725,804 A | 3/1998 | Yen |
| 5,770,570 A | 6/1998 | Paul et al. |
| 5,807,827 A | 9/1998 | Lee et al. |
| 5,840,733 A | 11/1998 | Krantz et al. |
| 5,843,440 A | 12/1998 | Pouletty et al. |
| 5,846,937 A | 12/1998 | Drucker |
| 5,855,866 A | 1/1999 | Thorpe et al. |
| 5,869,602 A | 2/1999 | Jonassen et al. |
| 5,874,408 A | 2/1999 | Nayar |
| 5,939,390 A | 8/1999 | Flodgaard et al. |
| 5,942,620 A | 8/1999 | Krantz et al. |
| 5,958,909 A | 9/1999 | Habener |
| 5,981,488 A | 11/1999 | Hoffmann |
| 6,006,753 A | 12/1999 | Efendic |
| 6,087,375 A | 7/2000 | Bridon et al. |
| 6,103,233 A | 8/2000 | Pouletty et al. |
| 6,107,489 A | 8/2000 | Krantz et al. |
| 6,133,235 A | 10/2000 | Galloway et al. |
| 6,191,102 B1 | 2/2001 | DiMarchi et al. |
| 6,268,343 B1 | 7/2001 | Knudsen et al. |
| 6,277,583 B1 | 8/2001 | Krantz et al. |
| 6,277,819 B1 | 8/2001 | Efendic |
| 6,277,863 B1 | 8/2001 | Krantz et al. |
| 6,284,725 B1 | 9/2001 | Coolidge et al. |
| 6,329,336 B1 | 12/2001 | Bridon et al. |
| 6,358,924 B1 | 3/2002 | Hoffmann |
| 6,403,324 B1 | 6/2002 | Krantz et al. |
| 6,437,092 B1 | 8/2002 | Ezrin et al. |
| 6,440,417 B1 | 8/2002 | Thibaudeau et al. |
| 6,500,918 B2 | 12/2002 | Ezrin et al. |
| 6,506,724 B1 | 1/2003 | Hiles et al. |
| 6,514,500 B1 | 2/2003 | Bridon et al. |
| 6,528,486 B1 | 3/2003 | Larsen et al. |
| 6,583,111 B1 | 6/2003 | DiMarchi et al. |
| 6,593,295 B2 | 7/2003 | Bridon et al. |
| 6,602,981 B2 | 8/2003 | Ezrin et al. |
| 6,610,825 B2 | 8/2003 | Ezrin et al. |
| 6,660,716 B1 | 12/2003 | Yakubu-Madus et al. |
| 6,703,359 B1 | 3/2004 | Young et al. |
| 6,706,689 B2 | 3/2004 | Coolidge et al. |
| 6,706,892 B1 | 3/2004 | Ezrin et al. |
| 6,723,530 B1 | 4/2004 | Drucker |
| 6,767,887 B1 | 7/2004 | Hoffmann et al. |
| 6,821,949 B2 | 11/2004 | Bridon et al. |
| 6,849,714 B1 | 2/2005 | Bridon et al. |
| 6,858,576 B1 | 2/2005 | Young et al. |
| 6,861,236 B2 | 3/2005 | Moll et al. |

(Continued)

FOREIGN PATENT DOCUMENTS

CA   2501421   11/2000

(Continued)

OTHER PUBLICATIONS

Davies et al., Drugs of the Future, 30(6):553-557, Jun. 2005.*

(Continued)

*Primary Examiner* — Marianne P Allen
(74) *Attorney, Agent, or Firm* — Morrison & Foerster LLP

(57) ABSTRACT

The present invention provides methods of administering an insulinotropic peptide in an amount effective to treat a disorder or condition while reducing nausea side effect by administering to a subject in need thereof an insulinotropic peptide conjugated to albumin. The present invention also provides methods of selecting a subject for administration of a conjugated insulinotropic peptide. Exemplary disorders or conditions treatable with an insulinotropic peptide include obesity and type II diabetes.

28 Claims, 18 Drawing Sheets

U.S. PATENT DOCUMENTS

Figure 1:
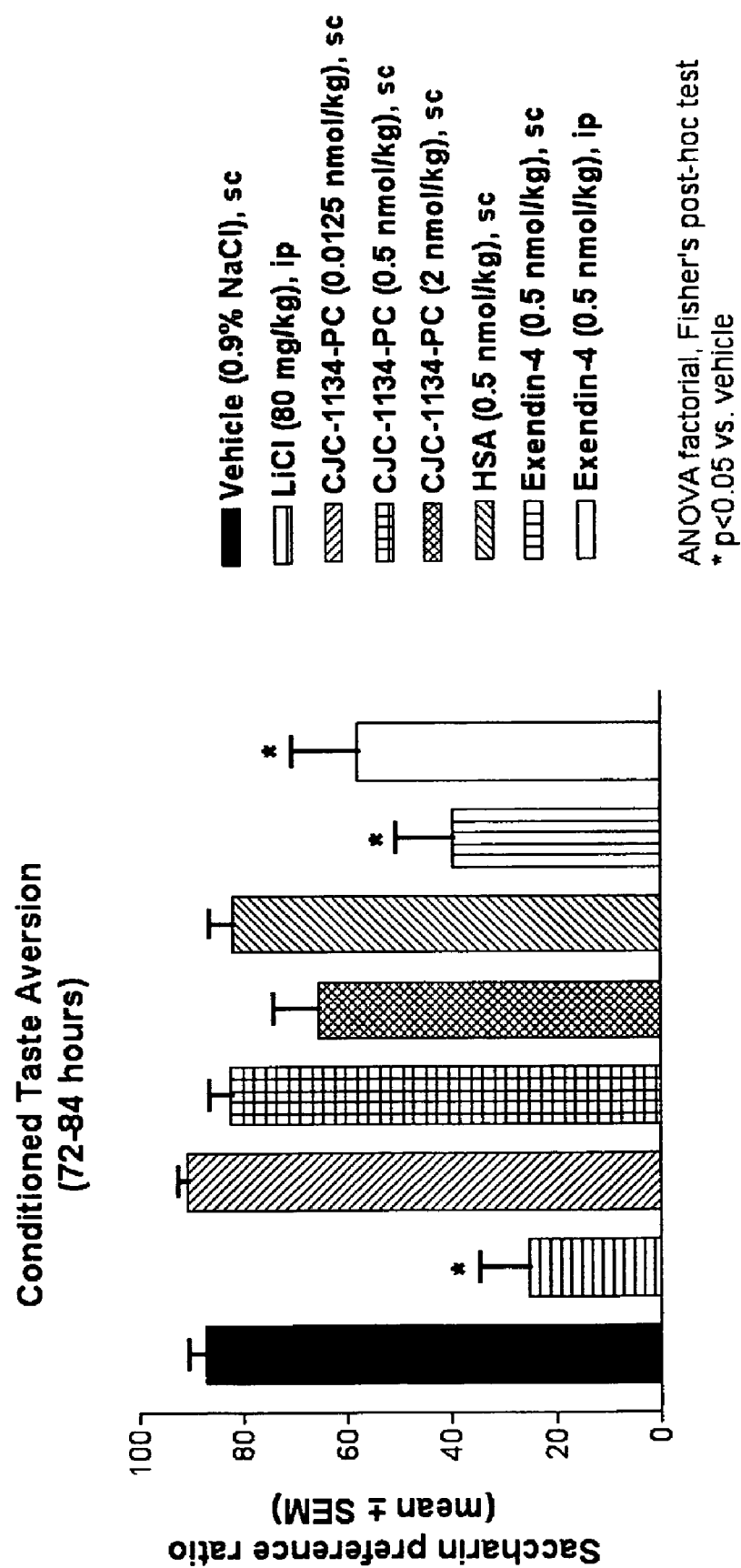

| | | | |
|---|---|---|---|
| 6,872,700 B1 | 3/2005 | Young et al. | |
| 6,887,470 B1 | 5/2005 | Bridon et al. | |
| 6,887,849 B2 | 5/2005 | Bridon et al. | |
| 6,894,024 B2 | 5/2005 | Coolidge et al. | |
| 6,902,744 B1 | 6/2005 | Kolterman et al. | |
| 6,924,264 B1 | 8/2005 | Prickett et al. | |
| 6,956,026 B2 | 10/2005 | Beeley et al. | |
| 6,989,366 B2 | 1/2006 | Beeley et al. | |
| 6,998,387 B1 | 2/2006 | Goke et al. | |
| 7,090,851 B1 | 8/2006 | Bridon et al. | |
| 7,101,843 B2 | 9/2006 | Glaesner et al. | |
| 7,105,508 B1 | 9/2006 | Kling et al. | |
| 7,112,567 B2 | 9/2006 | Bridon et al. | |
| 7,144,854 B1 | 12/2006 | Bridon et al. | |
| 7,166,695 B2 | 1/2007 | Krantz et al. | |
| 7,259,233 B2 * | 8/2007 | Dodd et al. | 530/308 |
| 2001/0018421 A1 | 8/2001 | Ezrin et al. | |
| 2001/0047084 A1 | 11/2001 | Knudsen et al. | |
| 2002/0009441 A1 | 1/2002 | Pouletty et al. | |
| 2002/0018751 A1 | 2/2002 | Bridon et al. | |
| 2002/0039999 A1 | 4/2002 | Ezrin et al. | |
| 2002/0049153 A1 | 4/2002 | Bridon et al. | |
| 2003/0073630 A1 | 4/2003 | Bridon et al. | |
| 2003/0108567 A1 | 6/2003 | Bridon et al. | |
| 2003/0108568 A1 | 6/2003 | Bridon et al. | |
| 2003/0170250 A1 | 9/2003 | Ezrin et al. | |
| 2003/0232754 A1 | 12/2003 | Holst et al. | |
| 2004/0053819 A1 | 3/2004 | Dodd et al. | |
| 2004/0127398 A1 | 7/2004 | Bridon et al. | |
| 2004/0138100 A1 | 7/2004 | Bridon et al. | |
| 2004/0156859 A1 | 8/2004 | Ezrin et al. | |
| 2004/0198654 A1 | 10/2004 | Glaesner et al. | |
| 2004/0248782 A1 | 12/2004 | Bridon et al. | |
| 2004/0266673 A1 | 12/2004 | Bakis et al. | |
| 2005/0037974 A1 | 2/2005 | Krantz et al. | |
| 2005/0065075 A1 | 3/2005 | Erickson et al. | |
| 2005/0070475 A1 | 3/2005 | Bridon et al. | |
| 2005/0176641 A1 | 8/2005 | Bakis et al. | |
| 2005/0176643 A1 | 8/2005 | Bridon et al. | |
| 2005/0187159 A1 | 8/2005 | Bridon et al. | |
| 2005/0267293 A1 | 12/2005 | Bousquet-Gagnon et al. | |
| 2006/0009377 A1 | 1/2006 | Bridon et al. | |
| 2006/0058235 A1 | 3/2006 | Bridon et al. | |
| 2006/0063699 A1 | 3/2006 | Larsen | |
| 2006/0069029 A1 | 3/2006 | Kolterman et al. | |
| 2006/0135426 A1 | 6/2006 | Bridon et al. | |
| 2006/0135428 A1 | 6/2006 | Bridon et al. | |
| 2006/0217304 A1 | 9/2006 | Bridon et al. | |
| 2006/0233707 A1 | 10/2006 | Kratz | |
| 2006/0252916 A1 | 11/2006 | DiMarchi et al. | |
| 2009/0075890 A1 | 3/2009 | Bridon et al. | |
| 2009/0093408 A1 | 4/2009 | Bridon et al. | |

FOREIGN PATENT DOCUMENTS

| | | |
|---|---|---|
| CA | 2434237 | 6/2002 |
| CA | 2550050 | 6/2005 |
| EP | 0602290 | 6/1994 |
| EP | 0969016 | 1/2000 |
| WO | WO 93/25579 | 12/1993 |
| WO | WO 96/06626 | 3/1996 |
| WO | WO 98/11126 | 3/1998 |
| WO | WO 99/24462 | 11/1998 |
| WO | WO 99/48536 | 9/1999 |
| WO | WO 00/69900 | 11/2000 |
| WO | WO 00/69902 | 11/2000 |
| WO | WO 00/70665 | 11/2000 |
| WO | WO 00/76550 | 12/2000 |

OTHER PUBLICATIONS

U.S. Appl. No. 09/623,533, filed Sep. 5, 2000, Bridon et al.

U.S. Appl. No. 09/623,543, filed Sep. 5, 2000, Bridon et al.

Adams et al., "Safety and Utilization of Blood Components as Therapeutic Delivery Systems," Curr. Pharm. Biotechnol., 4(5):275-282 (2003).

Akil et al., "Endogenous Opioids: Biology and Function," Ann. Rev. Neurosci., 7:223-255 (1984).

Baltzer et al., "The Addition of Ondansetron to the Combination of Metoclopramide, Dexamethasone, and Lorazepam Did Not Improve Vomiting Prevention in Patients Receiving High-Dose Cisplatin," Cancer, 73:730-723 (1994).

Baggio et al., "A Recombinant Human Glucagon-Like Protein (GLP)-1 Albumin Protein (Albugon) Mimics Peptidergic Activation of GLP-1 Receptor-Dependent Pathways Coupled With Satiety, Gastrointestinal Motility and Glucose Homeostasis," Diabetes, 53:2492-2500 (2004).

Barragan et al., "Interactions of exendin-(9-39) with the Effects of Glucagon-like Peptide-1-(7-36) Amide and of Exendin-4 on Arterial Blood Pressure and Heart Rate in Rats," Regulatory Peptides, 67:63-68 (1996).

Bell et al., "Hamster Preproglucagon Contains the Sequence of Glucagon and Two Related Peptides," Nature, 302:716-718 (1983).

Benhar et al., "Pseudomonas Exotoxin A Mutants," J. Biol. Chem., 269(18):13398-13404 (1994).

Bennett et al., "An Antiemetic Study Comparing Halcion to Ativan in Children Receiving Cancer Chemotherapy," Oncol. Nurs. Forum, 16(6):187A (1989).

Hirai et al., "A New Mast Cell Degranulating Peptide "mastoparan" in the Venom of Vespula Lewisii," Chem. Pharm. Bull., 27(8):1942-1944 (1979).

Holmes et al., "Site Specific 1:1 Opioid:Albumin Conjugate with in Vitro Activity and Long in Vivo Duration," Bioconjug. Chem., 11(4):439-444 (2000).

Hupe-Sodmann et al., "Endoproteolysis of Glucagon-like Peptide (GLP)-1(7-36) amide by Ectopeptidases in RINm5F Cells," Peptides, 18(5):625-632 (1997).

Ishikawa et al., "Enzyme-Labeling with Maleimides and Its Application to the Immunoassay of Peptide Hormones," Enzyme Labeled Immunoassay of Hormones and Drugs, Walter deGruyter & Co., Berlin, New York, pp. 43-57 (Oct. 7, 1978).

Isoai et al., "A Potent Anti-Metastatic Activity of Tumor Invasion-Inhibiting Factor-2 and Albumin Conjugate," Biochem. Biophys. Res. Commun., 192(1):7-14 (1993).

Iltz et al., "Exenatide: An Incretin Mimetic for the Treatment of Type 2 Diabetes Mellitus," Clin. Ther., 28(5):652-665 (2006).

Jette et al., "Human Growth Hormone-Releasing Factor $(hGRF)_{1-29}$ Albumin Bioconjugates Activate the GRF Receptor on the Anterior Pituitary in Rats: Identification of CJC-1295 as a Long-Lasting GRF Analog," Endocrinology, 146(7):3052-3058 (2005).

Kapas et al., "Cloning and Expression of cDNA Encoding a Rat Adrenomedullin Receptor," J. Biol. Chem., 270(43):25344-25347 (1995).

Kieffer et al., "The Glucagon-Like Peptides," Endocrine Rev., 20(6):876-913 (1999).

Kim et al., "Development and Characterization of a Glucagon-Like Peptide 1-Albumin Conjugate," Diabetes, 52:751-759 (2003).

Knusli et al., "Polyethylene Glycol (PEG) Modification of Granulocyte Macrophage Colony Stimulating Factor (GM-CSF) Enhances Neutrophil Priming Activity but not Colony Stimulating Activity," British Journal of Haematology, 82:654-663 (1992).

Kolodny et al., "A Conjugation of Synthetic Peptides to Proteins: Quantitation from S-Carboxymethylcysteine Released Upn Acid Hydrolysis," Analytical Biochemistry, 187:136-140 (1990).

Leger et al., "Synthesis and In Vitro Analysis of Atrial Natriuretic Peptide-Albumin Conjugates," Bioorganic & Medicinal Chemistry Letters, 13:3571-3575 (2003).

Leger et al., "Identification of CJC-1131-Albumin Bioconjugate as a Stable and Bioactive GLP-1(7-36) Analog," Bioorganic & Medicinal Chemistry Letters, 14:4395-4398 (2004).

Lindley et al., "Quality of Life Consequences of Chemotherapy-Induced Emesis," Qual. Life Res., 1:331-340 (1992).

Lopez et al., "Mammalian Pancreatic Preproglucagon Contains Three Glucagon-related Peptides," Proc. Natl. Acad. Sci. USA, 80:5485-5489 (1983).

Mao et al., "Superoxide Dismutase: Improving Its Pharmacological Properties by Conjugation with Human Serum Albumin," Biomat. Art. Cells, Art. Org., 17(3):229-244 (1989).

Marburg et al., "Introduction of the Maleimide Function onto Resin-Bound Peptides: A Simple, High Yield Process Useful for Discriminating among Several Lysines," Bioconjug. Chem., 7:612-616 (1996).

Meurer et al., "Properties of Native and In Vitro Glycosylated Forms of the Glucagon-like Peptide-1 Receptor Antagonist Exendin (9-39),"Metabolism, 48(6):716-724 (1999).
Mumby et al., "Antisera of Designed Specificity for Subunits of Guanine Nucleotide-binding Regulatory Proteins," Proc. Natl. Acad. Sci., 83:265-269 (1986).
Nauck et al., "Glucagon-like Peptide 1 and its Derivatives in the Treatment of Diabetes," Regulatory Peptides, 128:135-148 (Jun. 15, 2005).
Bergmann et al., "Cationized Serum Albumin Enhances Response of Cultured Fetal Rat Long Bones to Parathyroid Hormone," Endocrinology, 116(5):1729-1733 (1985).
Bhargava et al., "Immobilization of Active Urokinase on Albumin Microspheres: Use of a Chemical Dehydrant and Process Monitoring," Pharmaceutical Research, 9(6):776-781 (1992).
Breton et al., "Prolonged Half-Life in the Circulation of a Chemical Conjugate Between a Pro-Urokinase Derivative and Human Serum Albumin," Eur. J. Biochem., 231(3):563-569 (1995).
Calara et al., "A Randomized, Open-Label, Crossover Study Examining the Effect of Injection Site on Bioavailability of Exenatide (Synthetic Exendin-4)," Clin. Ther., 27(2):210-214 (2005).
Conjuchem Press Release, "ConjuChem Hits Primary End-point in Monotherapy Phase II Clinical Trial with DAC™: GLP-1" (Jul. 14, 2004).
Conjuchem Press Release, "ConjuChem Provides Clinical Update on DAC™: GLP-1 and PC-DAC™: Exendin-4" (Sep. 30, 2005).
Conjuchem Press Release, "ConjuChem to Initiate Phase I/II Clinical Study of PC-DAC™: Exendin-4 for Type 2 Diabetes" (Feb. 27, 2006).
Conjuchem Press Release, "Phase I/II Preliminary Results of PC-DAC™: Exendin-4 Trial for Type 2 Diabetes Demonstrate Excellent Tolerability and Positive Efficacy" (Apr. 26, 2006).
Conjuchem Press Release, "Final Results of PC-DAC™: Exendin-4 phase I/II Trial for Type 2 Diabetes Confirm Excellent Tolerability, Positive Efficacy, and Extended Duration of Activity" (Sep. 12, 2006).
Cotanch, "Relaxation Training for Control of Nausea and Vomiting in Patients Receiving Chemotherapy," Cancer Nurs., 6:277-283 (1983).
Davis et al., "Reduction of Immunogenicity and Extension of Circulating Half-Life of Peptides and Proteins," Peptide and Protein Drug Delivery, Lee, V. H. L., ed., Marcel Dekker, Inc., NY, NY; 831-864 (1991).
Delgado et al., "The Uses and Properties of PEG-Linked Proteins," Critical Reviews in Therapeutic Drug Carrier Systems, 9(3,4):249-304 (1992).
Drucker, "Perspectives in Diabetes," Diabetes, 47(2):159-169 (Feb. 1998).
Edwards et al., "Glucagon-like Peptide I Has a Physiological Role in the Control of Postprandial Glucose in Humans," Diabetes, 48:86-93 (1999).
Edwards et al., "Exendin-4 Reduces Fasting and Postprandial Glucose and Decreases Energy Intake in Healthy Voluneers," Am. J. Physiol. Endocrinol. Metab., 281:E155-E161 (2001).
Eng et al., "Prolonged Effect of Exendin-4 on Hyperglycemia of db/db Mice," J. Biol. Chem., 267(11):7402-7405 (1992).
Eng, "Isolation and Characterization of Exendin-4, an Exendin-3 Analogue, from Heloderma suspecum Venom," Diabetes, 45:152A (abstract 554) (1996).
Foa et al., "Glucagon and Other Products of the Proglucagon Gene: Physiology and Possible Role in the Pathogenesis of Disease," Giomale Italiano Di Diabetologia, 11:(Supplemental)1-42 (1991).
Francis et al., "PEGylation of Cytokines and other Therapeutic Proteins and Peptides: The Importance of Biological Optimisation of Coupling Techniques," International Journal of Hematology, 68:1-18 (1998).
Gombotz et al., "Biodegradable Polymers for Protein and Peptide Drug Delivery," Bioconjug. Chem., 6:332-351 (1995).
Goodson et al., "Site-Directed Pegylation of Recombinant Interleukin-2 at Its Glycosylation Site," Bio/Technology, 8:343-346 (1990).
Goosen, "Optimization of Microencapsulation Parameters: Semipermeable Microcapsules as a Bioartificial Pancreas," Biotechnology and Bioengineering, XXVII:146-150 (1985).

Heinrich et al., "Pre-proglucagon Messenger Ribonucleic Acid: Nucleotide and Encoded Amino Acid Sequences of the Rat Pancreatic Complementary Deoxyribonucleic Acid," Endocrinology, 115:2176-2181 (1984).
Oren et al., "Mode of Action of Linear Amphipathic α-Helical Antimicrobial Peptides," Biopolymers (Peptide Science), 47:451-463 (1998).
Paige et al., "Prolonged Circulation of Recombinant Human Granulocyte-Colony Stimulating Factor by Covalent Linkage to Albumin Through a Heterobifunctional Polyethylene Glycol," Pharm. Res., 12(12): 1883-1888 (1995).
Patrias et al., "Trimethylaminuria (Fish-Malodor Syndrome) and the Flavin Monooxygenases," Biotech Report, 106-107 (1994/1995).
Poznansky, "Enzyme-Protein Conjugates: New Possibilities for Enzyme Therapy," Pharmac. Ther., 21:53-76 (1983).
Poznansky et al., "Growth Hormone-Albumin Conjugates Reduced Renal Toxicity and Altered Plasma Clearance," FEBS Letters, 239(1):18-22 (1988).
Qu et al., "A Role for Melanin-Concentrating Hormone in the Central Regulation of Feeding Behaviour," Nature, 380:243-247 (1996).
Raufman, "Bioactive Peptides from Lizard Venoms," Regulatory Peptides, 61:1-18 (1996).
Reubi et al., "Specific High Affinity Binding Sites for Somatostatin-28 on Pancreatic β-Cells: Differences with Brain Somatostatin Receptors," Endocrinology, 110(3):1049-1051 (1982).
Rhodes et al., "Sensory Perception of Patients on Selected Antineoplastic Chemotherapy Protocols," Cancer Nurs., 17:45-51 (1994).
Ringsdorf, "Structure and Properties of Pharmacologically Active Polymers," J. Polymer Sci. Symposium No. 51, pp. 135-153 (1975).
Ritzel et al., "Pharmacokinetic, Insulinotropic, and Glucagonostatic Properties of GLP-1 [7-36 amide] after Subcutaneous Injection in Healthy Volunteers. Dose-response-relationships," Diabetologia, 38:720-725 (1995).
Ritzel et al., "A Synthetic Glucagon-like Peptide-1 Analog with Improved Plasma Stability," Journal of Endocrinology, 159:93-102 (1998).
Robberecht et al., "Immunoreactive Helodermin-like Peptides in Rat: A New Class of Mammalian Neuropeptides Related to Secretin and VIP," Biochem. Biophys. Res. Commun., 130(1):333-342 (1985).
Ruiz-Grande et al., "Lipolytic Action of Glucagon-like Peptides in Isolated Rat Adipocytes," Peptides, 13(1)13-16 (1992).
Santiago, "Incidence of IDDM and Frequency of the DQβ1 and DQα1," Diabetes, Abstract book, 56th Annual Meeting and Scientific Sessions, 847 (Jun. 8-11, 1996).
Schirra ct al., "Exendin(9-39)amide is an Antagonist of Glucagon-like Peptide-1(7-36)amide in Humans," J. Clin. Invest., 101(7):1421-1430 (1998).
Selkoe, "Physiological Production of the β-Amyloid Protein and the Mechanism of Alzheimer's Disease," TINS, 16(10):403-409 (1993).
Siegel et al., "Biological Activity of GLP-1 Analogues with N-Terminal Modifications," Regulatory Peptides, 79(23):93-102 (1999).
Smith et al., "Atrial Natriuretic Factor During Fetal and Postnatal Life: A Review," J. Dev. Physiol., 12:55-62 (1989).
Stehle et al., "The Loading Rate Determines Tumor Targeting Properties of Methotrexate-Albumin Conjugates in Rats," Anti-Cancer Drugs, 8:677-685 (1997).
Sung et al., "A Double-Blind, Placebo-Controlled Pilot Study Examining the Effectiveness of Intravenous Ondansetron in the Prevention of Postoperative Nausea and Emesis," J. Clin Anesthes., 5:22-29 (1993).
Syed et al., "Potent Antithrombin Activity and Delayed Clearance from the Circulation Characterize Recombinant Hirudin Genetically Fused to Albumin," Blood, 89(9):3243-3252 (1997).
Thibaudeau et al., "Synthesis and Evaluation of Insulin-Human Serum Albumin Conjugates," Bioconjug. Chem., 16:1000-1008 (2005).
Thim et al., "Molecules in Focus: CART, a New Anorectic Peptide," Int. J. Biochem. Cell. Biol., 30:1281-1284 (1998).
Turton et al., "A Role for Glucagon-like-Peptide-1 in the Central Regulation of Feeding," Nature, 379:69-72 (1996).
Vilaseca et al., "Protein Conjugates of Defined Structure: Synthesis and Use of a New Carrier Molecule," Bioconjug. Chem., 4:515-520 (1993).

Yeh et al., "Design of Yeast-Secreted Albumin Derivates for Human Therapy: Biological and Antiviral Properties of a Serum Albumin-CD4 Genetic Conjugate," Proc. Natl. Acad. Sci. USA, 89:1904-1908 (1992).

Young et al., "Glucose-Lowering and Insulin-Sensitizing Actions of Exendin-4," Diabetes, 48:1026-1034 (1999).

Zalipsky, "Functionalized Poly(ethylene glycol) for Preparation of Biologically Relevant Conjugates," Bioconjug. Chem., 6:150-165 (1995).

Zegers et al., "An Improved Conjugation Method for Controlled Covalent Coupling of Synthetic Peptides to Proteins Using Glutaraldehyde in a Dialysis Method," Journal of Immunological Methods, 130:195-200 (1990).

Amylin Pharmaceuticals, Inc., "United States Securities and Exchange Commission, Form 10K, Annual Report Pursuant to Section 13 or 15(d) of the Securities Exchange Act of 1934, for the Fiscal Year Ended Dec. 31, 1999."

Banks et al., "Brain Uptake of the Glucagon-Like Peptide-1 Antagonist Exendin(9-39) After Intranasal Administration," Pharmacol Exp Ther. 309(2):469-475 (May 2004).

Cefalu, "Concept, Strategies, and Feasibility of Noninvasive Insulin Delivery," Diabetes Care 27:239-246, (Jan. 2004).

Kinzig et al., "The Diverse Roles of Specific GLP-1 Receptors in the Control of Food Intake and the Response to Visceral Illness," J Neurosci. 22(23):10470-10476 (Dec. 2002).

Harlow & Lane, 1988, "Antibodies: A Laboratory Manual," Cold Spring Harbor Laboratory Press, Cold Spring Harbor, N.Y., pp. 101, 129.

* cited by examiner

Effect of CJC-1134-PC and exendin-4 on body weight gain and food intake in diabetic obese rats: cumulative % weight gain versus Day 1.

Effect of CJC-1134-PC and exendin-4 on body weight gain and food intake in diabetic obese rats: cumulative food intake from Day 1.

METHOD OF TREATMENT OF DIABETES AND/OR OBESITY WITH REDUCED NAUSEA SIDE EFFECT

This application claims benefit under 35 U.S.C. §119(e) of U.S. Provisional Application No. 60/735,404, filed Nov. 9, 2005, which is hereby incorporated by reference in its entirety.

1. FIELD OF THE INVENTION

The present invention provides methods of administering an insulinotropic peptide in an amount effective to treat a disorder or condition while reducing nausea. Exemplary disorders or conditions treatable with an insulinotropic peptide include obesity and type II diabetes.

2. BACKGROUND OF THE INVENTION

The prevalence of diabetes for all age groups worldwide was estimated to be 2.8%, or 171 million in 2000, and is projected to be 4.4%, or 366 million in 2030. See Wild et al., 2004, *Diabetes* Care 27(5): 1047-1053. In the United States alone, the prevalence of diabetes mellitus in 2005 was estimated at 20.8 million, or roughly 7% of the U.S. population. See Centers for Disease Control and Prevention, 2005, *National Diabetes Fact Sheet: General Information and National Estimates on Diabetes in the United States*, 2005. Approximately 95% of all patients with diabetes mellitus have type II disease. Diabetes is currently the fifth leading cause of death in the United States and is associated with excess morbidity stemming from cardiovascular disease, kidney failure, blindness, and lower limb amputation.

Similarly, obesity is a condition increasingly affecting the population worldwide. According to the World Health Organization, in 1995 there were an estimated 200 million obese adults worldwide and another 18 million under-five children classified as overweight. As of 2000, the number of obese adults had increased to over 300 million. See Formiguera et al., 2004, *Best Practice & Research Clinical Gastroenterology*, 18:6, 1125-1146.

The insulinotropic peptides glucagon-like peptide (GLP-1), exendin-3 and exendin-4 have been investigated as possible therapeutic agents for the management of type II non-insulin-dependent diabetes mellitus as well as related metabolic disorders, such as obesity. GLP-1 is a proglucagon-derived peptide secreted from intestinal L-cells in response to nutrient ingestion. GLP-1 acts as an incretin to lower post-prandial glycemic excursion via stimulation of insulin secretion and inhibition of glucagon secretion. GLP-1 also exerts actions independent of islet hormone secretion, including inhibition of both gastric emptying and food intake and stimulation of β-cell proliferation. As GLP-1 agonists, exendin-3 and exendin-4 mimic the actions of naturally occurring GLP-1 and are therefore classified as incretin mimetics.

While useful, GLP-1, exendin-3 and exendin4 can present limited duration of action associated with short plasma half-lives in vivo, mainly due to rapid serum clearance and proteolytic degradation by dipeptidyl peptidase-IV. In addition, administration of these peptides for the treatment of diabetes or obesity can result in nausea side effect. Subcutaneous injection of GLP-1 at high doses (1.5 nmol/kg body weight and higher) lead to nausea and, less often, vomiting in a significant proportion of subjects exposed to treatment. See Ritzel et al., 1995, *Diabetologia* 38:720-725. Further, in three phase III comparative efficacy trials of exenatide, the synthetically derived peptide of exendin-4, nausea was the most commonly reported adverse event, with an incidence of 43.5% of the 1446 enrolled patients enrolled in all three studies. See Iltz et al, 2006, *Clin. Ther*. 28(5): 652-665.

Thus, there is a need for administration of forms of GLP-1, exendin-3, exendin-4, and other insulinotropic peptides which minimize side effects such as nausea and vomiting, but maintain their therapeutic advantages.

3. SUMMARY OF THE INVENTION

The present invention is based, in part, on the discovery that administration to a subject of an insulinotropic peptide conjugated to albumin can prevent, reduce, or eliminate nausea side effect compared to administration of the insulinotropic peptide alone. Accordingly, the present invention provides methods of administering to a subject a form of an insulinotropic peptide that prevents, reduces, or eliminates nausea side effect compared to administration of the insulinotropic peptide alone. In certain embodiments the insulinotropic peptide is in the form of a conjugate. In some embodiments the insulinotropic peptide is in the form of an insulinotropic peptide conjugated to a macromolecule. In some embodiments the insulinotropic peptide is in the form of an insulinotropic peptide conjugated to albumin.

In certain embodiments, the methods of the invention comprise the step of administering to the subject an insulinotropic peptide conjugated to albumin that can prevent, reduce, or eliminate nausea side effect that may accompany administration of the unconjugated insulinotropic peptide. In some embodiments, administration of the conjugated insulinotropic peptide prevents nausea side effect compared to administration of the unconjugated insulinotropic peptide. In some embodiments, administration of the conjugated insulinotropic peptide reduces nausea side effect compared to administration of the unconjugated insulinotropic peptide. In some embodiments, administration of the conjugated insulinotropic peptide eliminates nausea side effect compared to administration of the unconjugated insulinotropic peptide. In some embodiments, the amount administered is effective to prevent, reduce, or eliminate nausea side effect in the subject.

While not intending to be bound by any particular theory of operation, it is believed that an effective approach to prevent, reduce, or eliminate the incidence of nausea that can accompany the administration of an insulinotropic peptide is to identify a patient population having a sensitivity to nausea before, during or after treatment with an insulinotropic peptide. Accordingly, the patient population can be treated with reduced nausea by administration of an insulinotropic peptide conjugated to albumin as described herein.

In certain embodiments, the present invention provides methods of selecting a population, for example a sub-population, of subjects suitable for treatment with the insulinotropic peptide conjugated to albumin. Exemplary methods of selection are described herein.

In certain embodiments, the methods of the invention comprise the step of administering to the subject an amount of conjugated insulinotropic peptide effective for treating a disorder or condition while providing reduced nausea side effect. Exemplary conditions or disorders treatable with insulinotropic peptides include, but are not limited to, obesity and diabetes, including maturity onset diabetes mellitus (type II diabetes).

The insulinotropic peptide of the present invention can be any insulinotropic peptide known to those of skill in the art. For example it can be any peptide which stimulates, or causes the stimulation of, the synthesis or expression of the hormone insulin. In some embodiments the insulinotropic peptide is selected from the group consisting of glucagon-like peptide 1, exendin-3 and exendin-4, and their precursors, derivatives, or fragments.

The conjugated insulinotropic peptide of the present invention can be conjugated to a macromolecule. In some embodiments, the insulinotropic peptide is conjugated to albumin. In some embodiments, the insulinotropic peptide is conjugated to serum albumin. In some embodiments, the insulinotropic peptide is conjugated to human serum albumin. In some embodiments, the insulinotropic peptide is conjugated to recombinant serum albumin. In some embodiments, the insulinotropic peptide is conjugated to recombinant human serum albumin.

The conjugated insulinotropic peptide of the present invention can be administered in a pharmaceutically acceptable formulation by any route known to those of skill in the art, including but not limited to oral, intranasal, intravascular, intraarterial, intramuscular, subcutaneous, transdermal or rectal administration.

In another aspect, the present invention provides methods of selecting a subject for treatment with an insulinotropic peptide conjugated to albumin. In certain embodiments, the methods comprise the step of identifying a subject having a condition or disorder treatable with an insulinotropic peptide who is prone to experiencing, has experienced, or is experiencing nausea. The subject is selected for treatment when the subject is prone to experiencing, has experienced, or is experiencing nausea as determined by any method known to those of skill in the art without limitation. Exemplary methods are described herein.

In further aspect, the present invention provides methods of administering an insulinotropic peptide. In certain embodiments, the methods comprise the step of selecting a nausea-sensitive subject having a disorder or condition treatable with the insulinotropic peptide and administering to the subject the insulinotropic peptide conjugated to albumin in an amount effective to treat the disorder or condition, wherein the conjugated insulinotropic peptide prevents, reduces, or eliminates nausea compared to the administration of unconjugated insulinotropic peptide. The methods of selecting a subject who is prone to experiencing has experienced or is experiencing nausea are described herein.

4. BRIEF DESCRIPTION OF THE FIGURES

Figure 2:
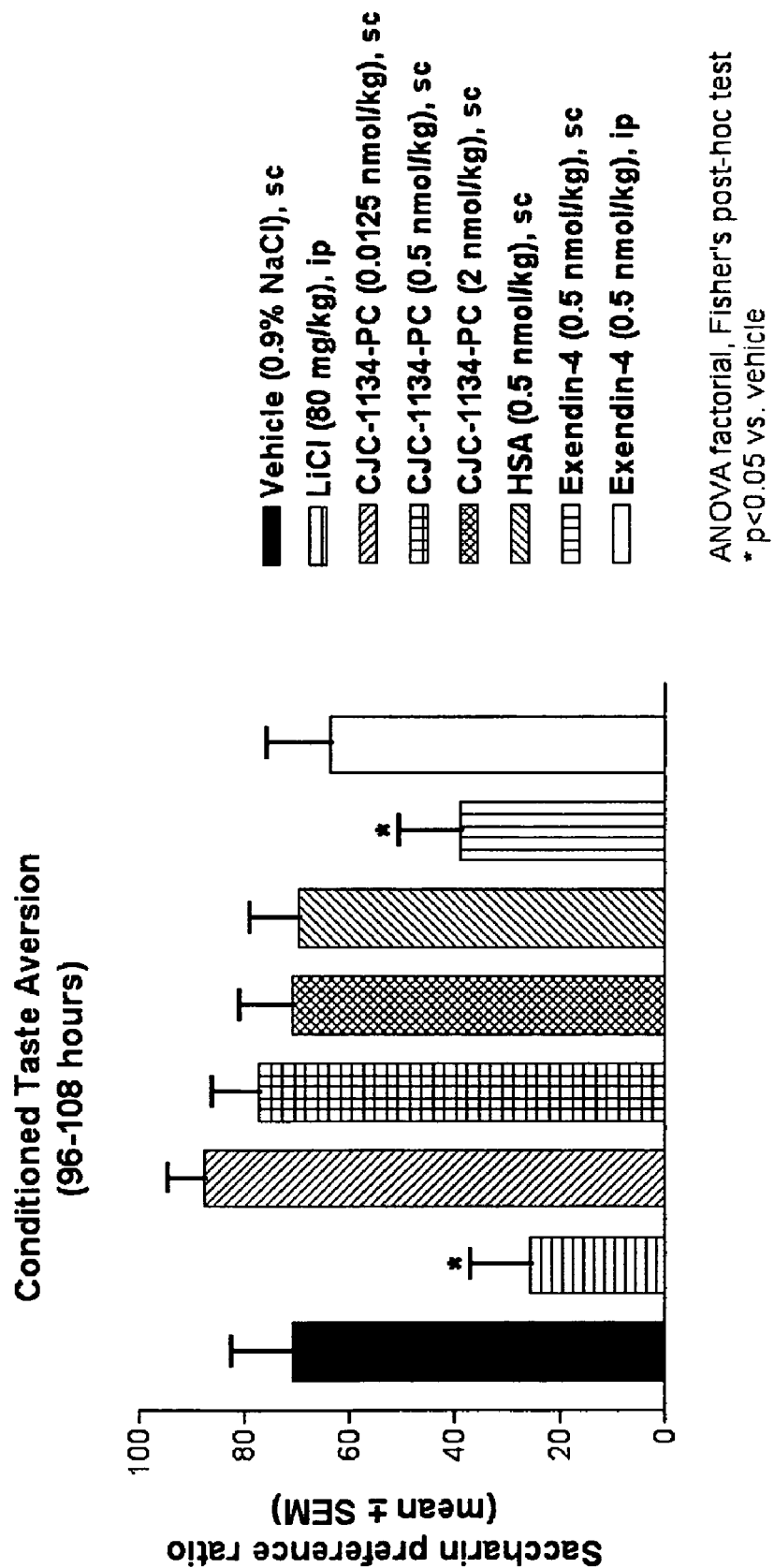
Figure 3:
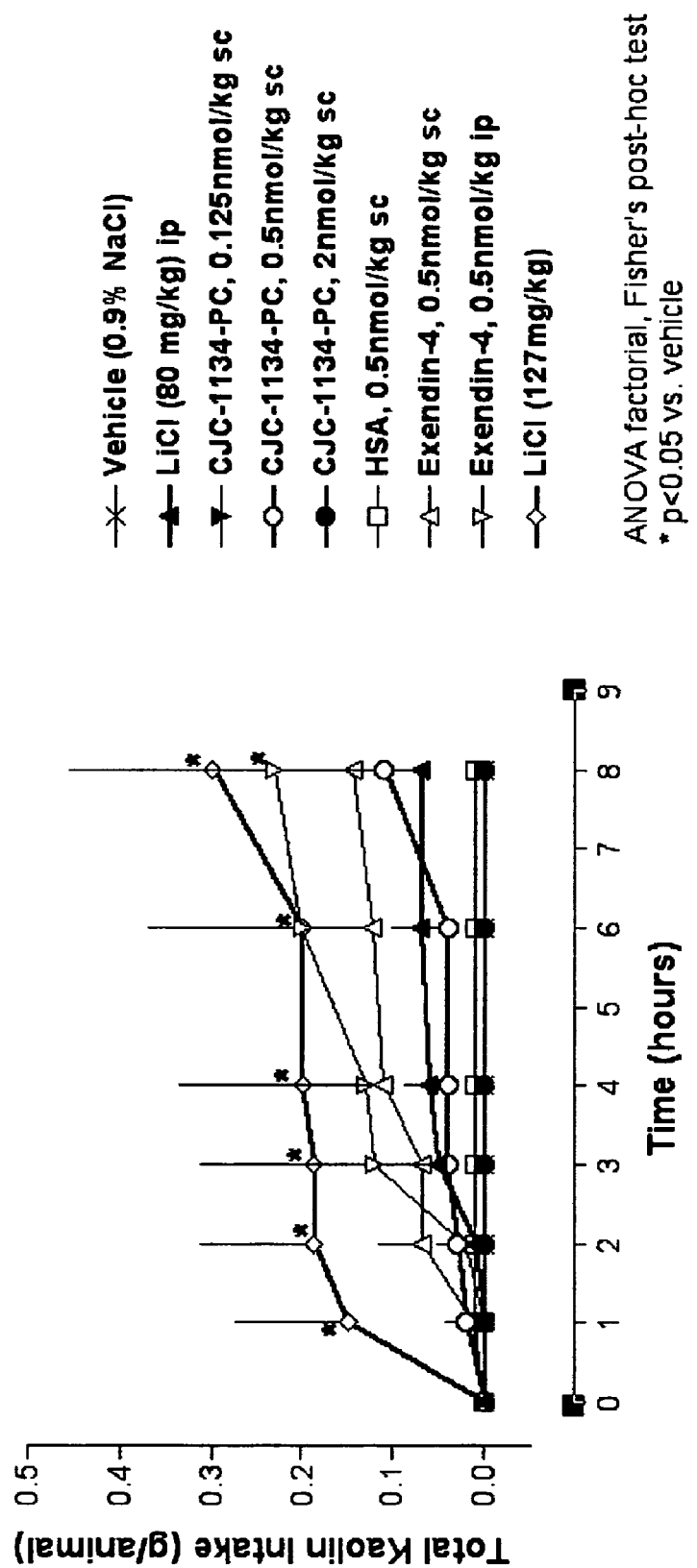
Figure 4:
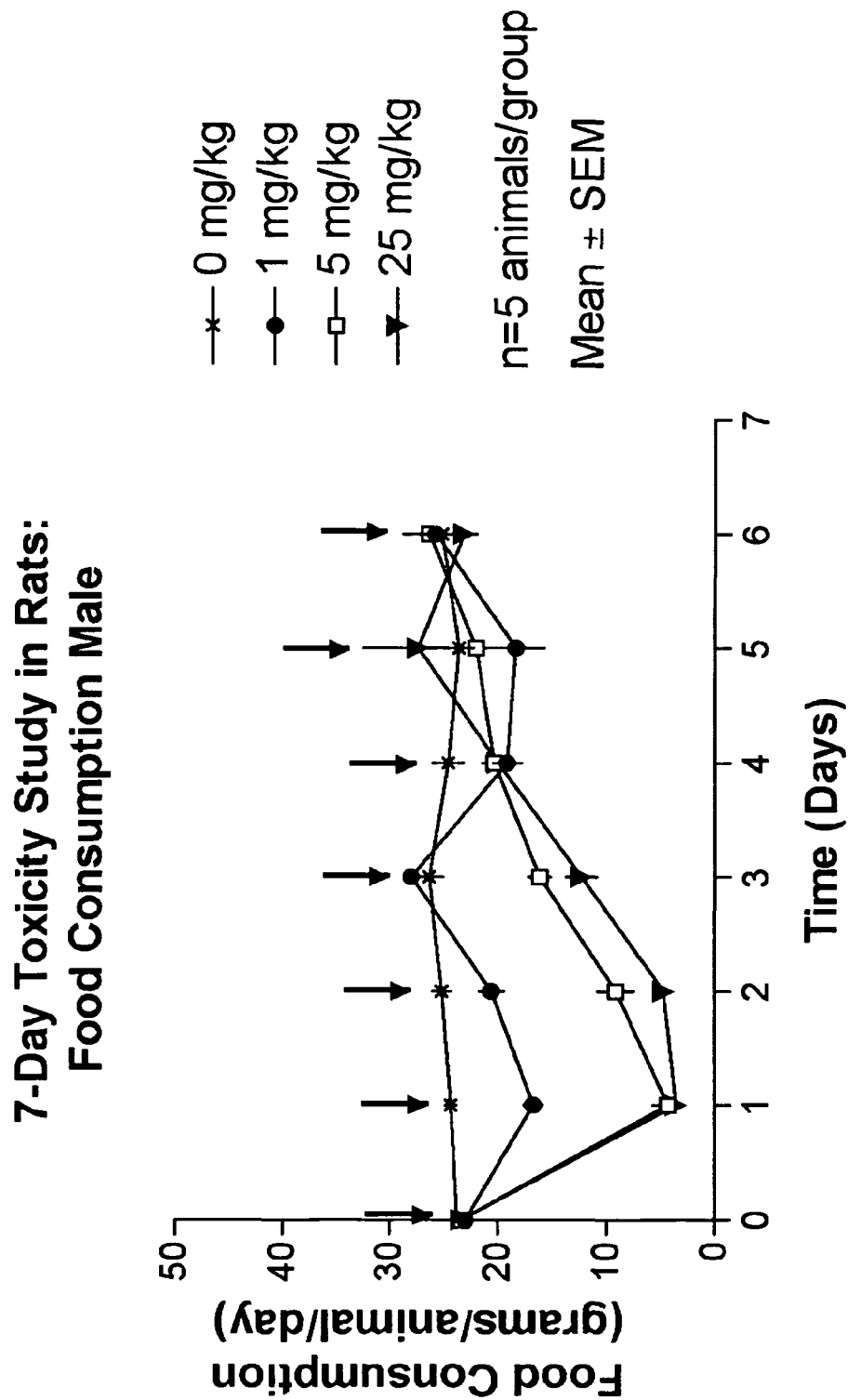
Figure 5:
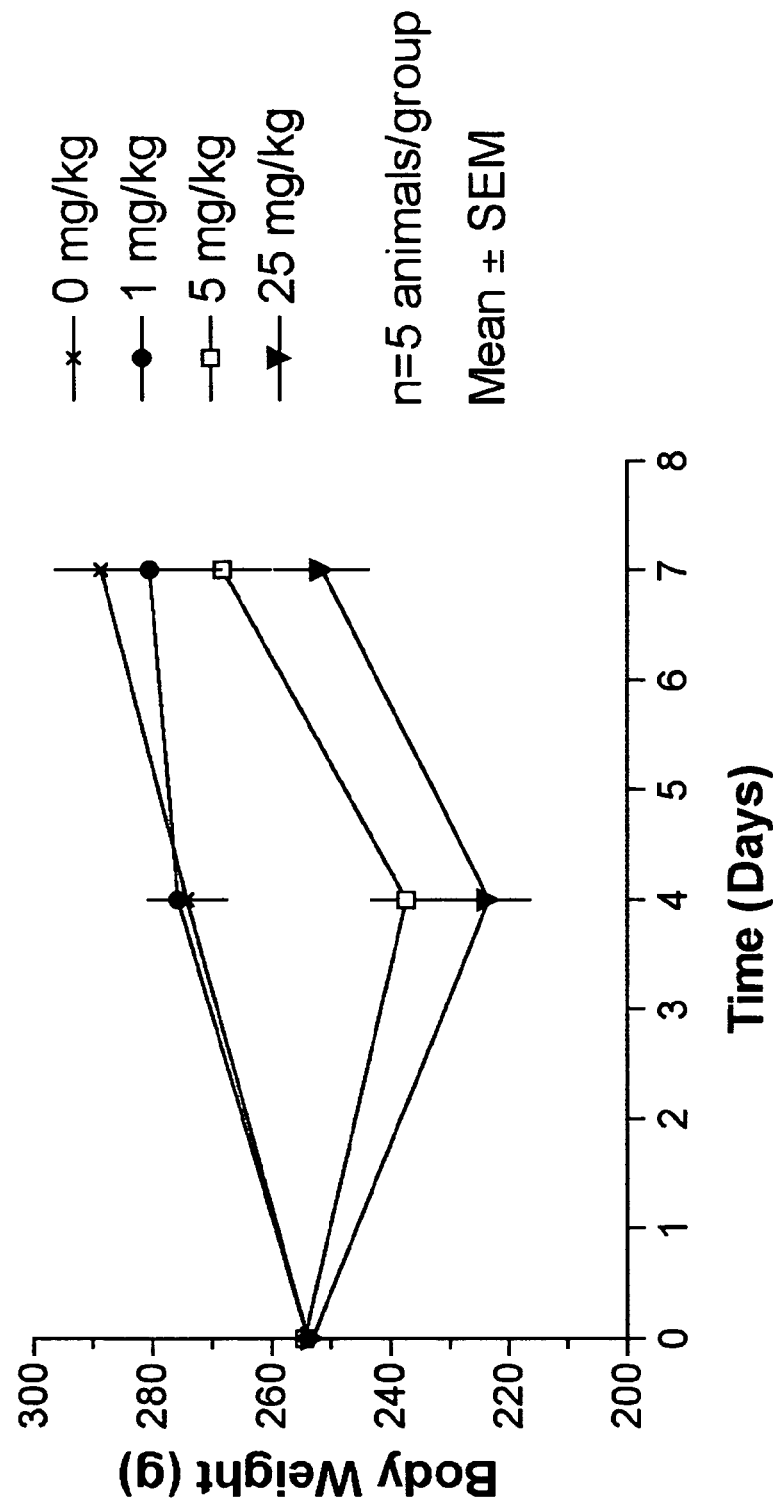
Figure 6:
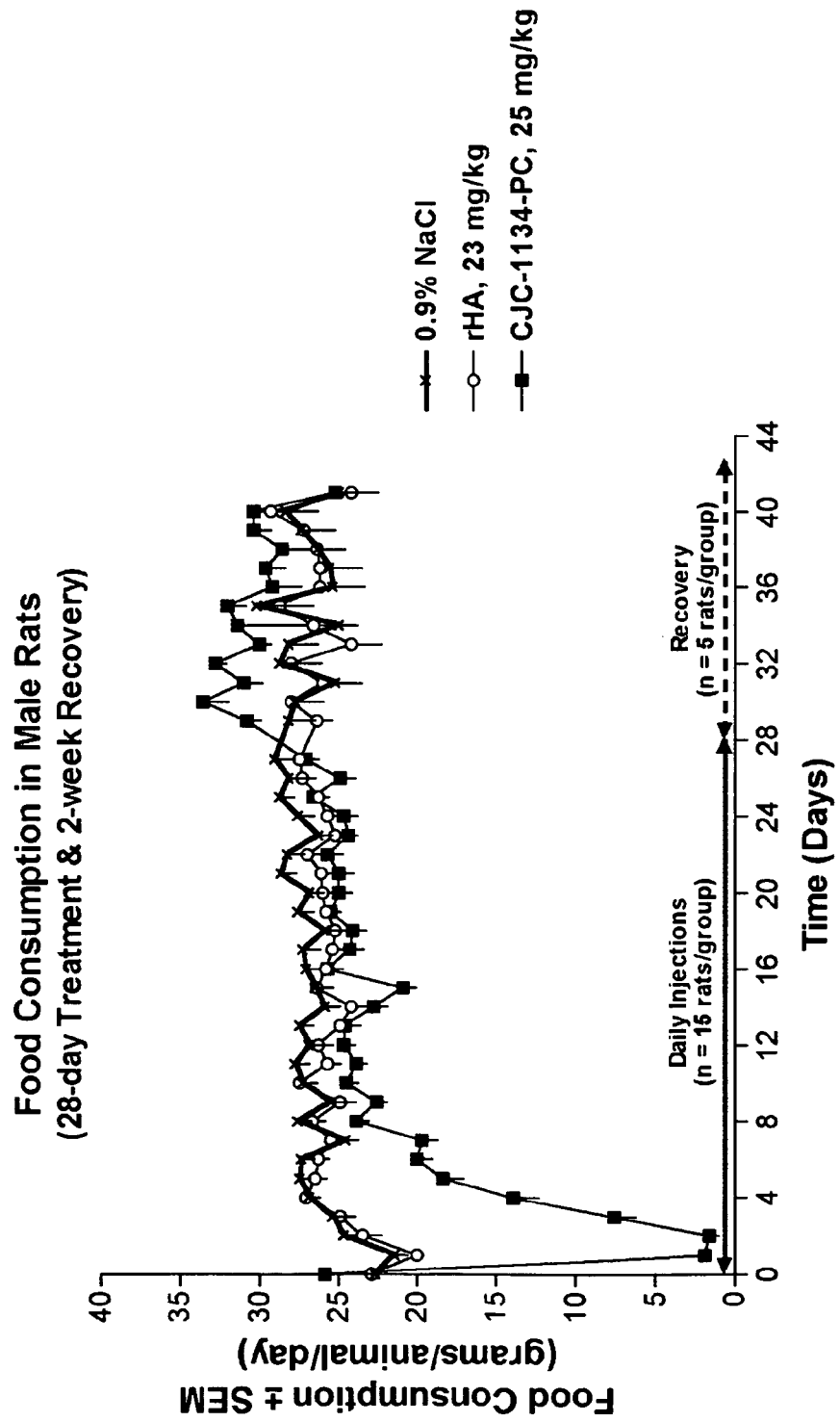
Figure 7:
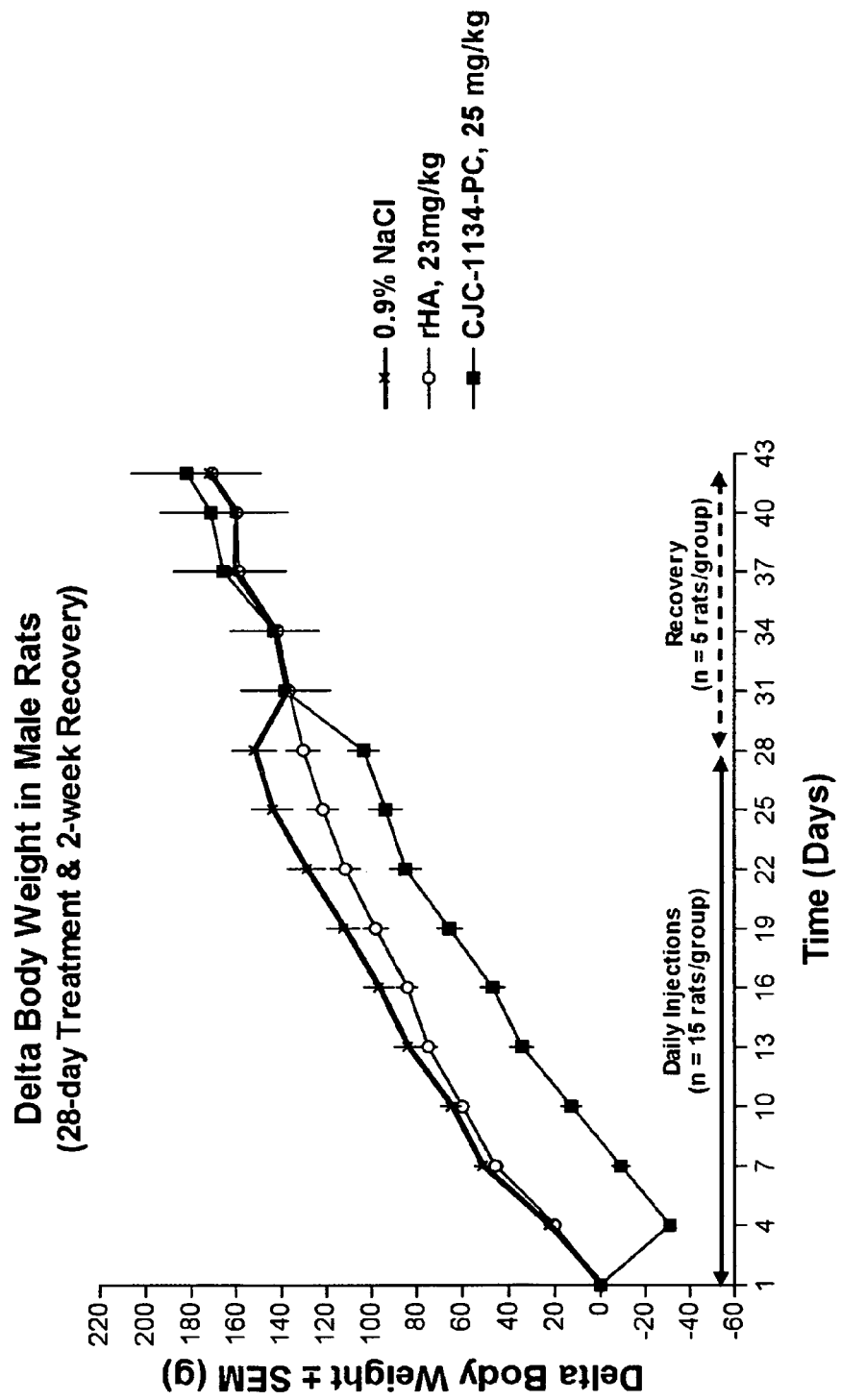
Figure 8:
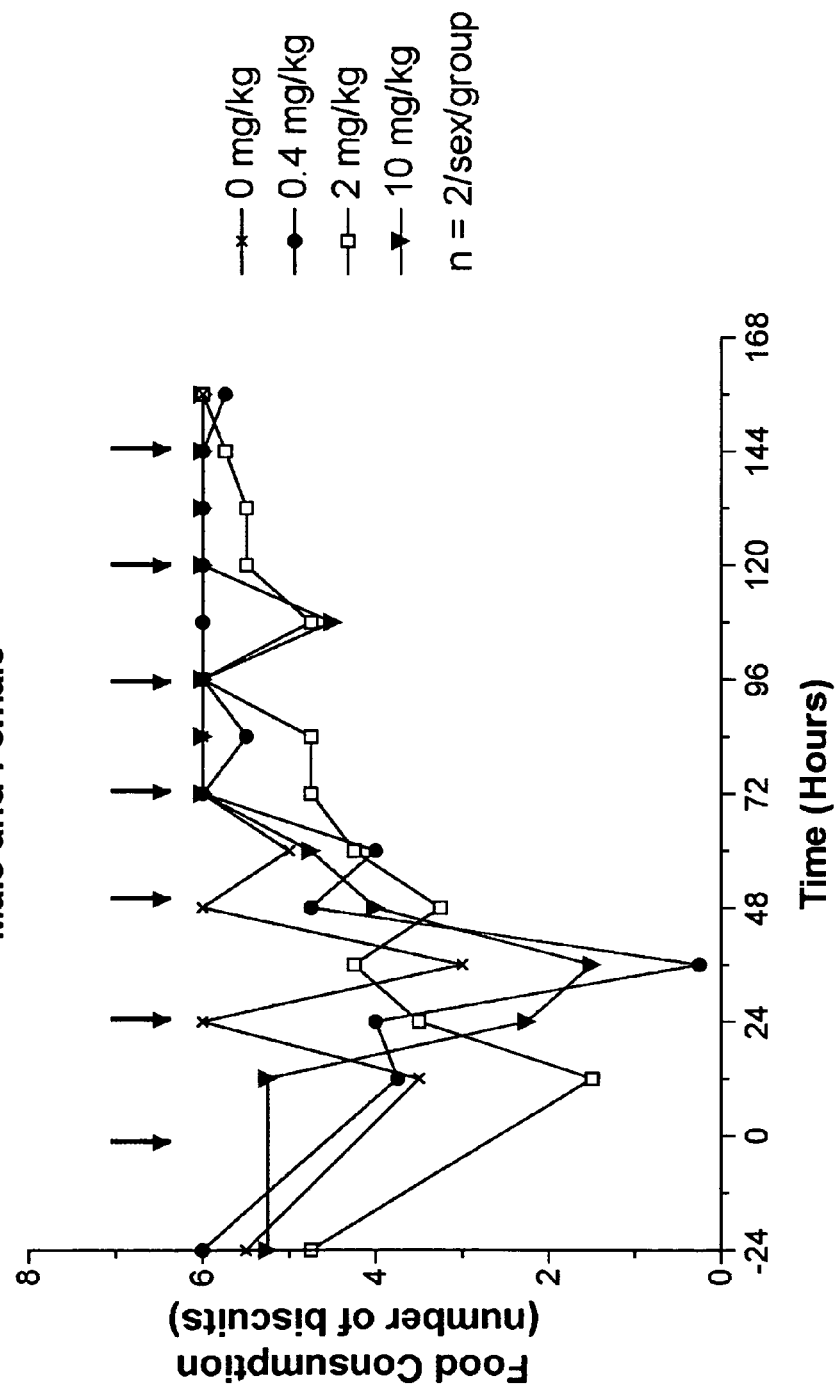
Figure 9:
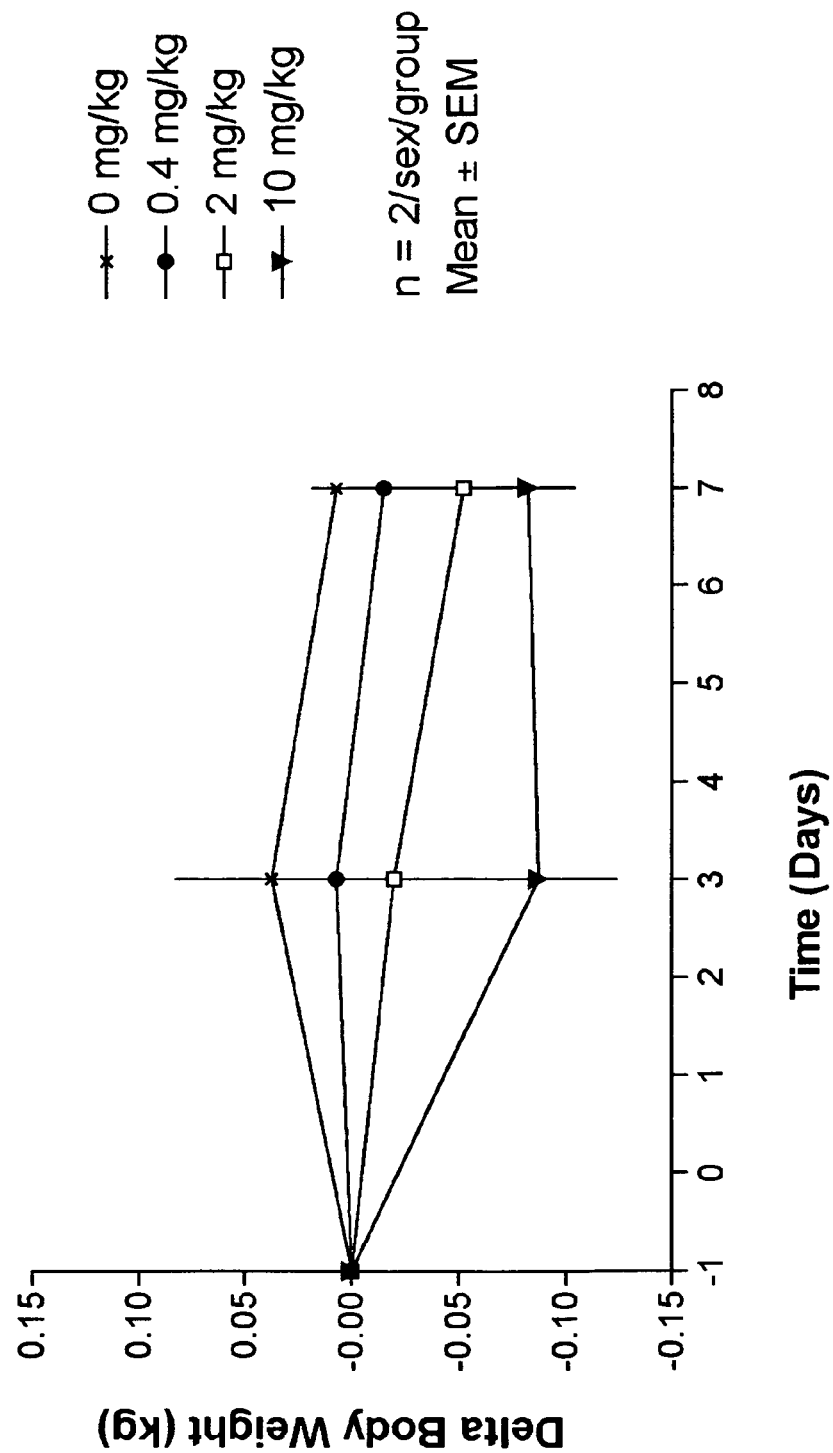
Figure 10:
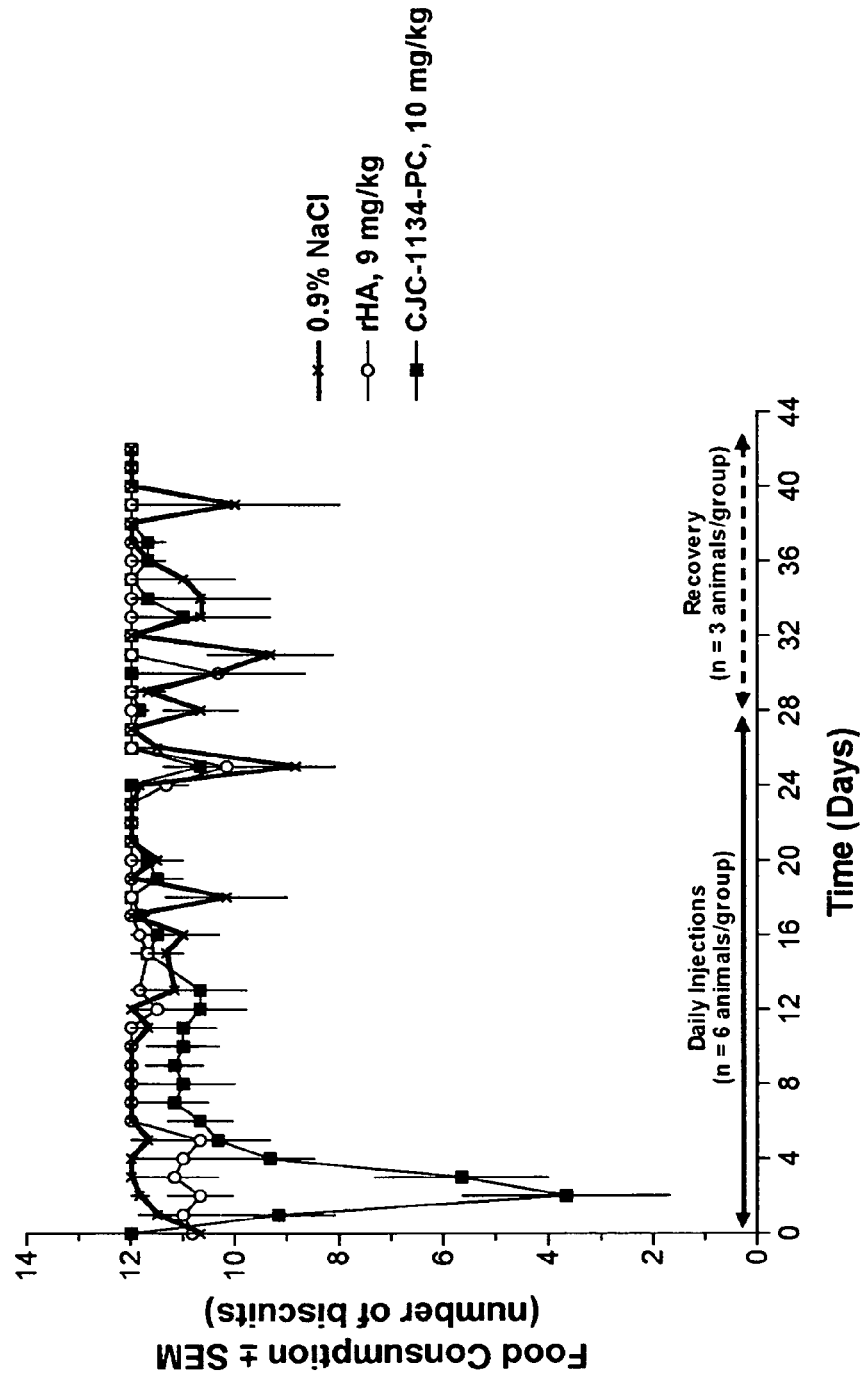
Figure 11:
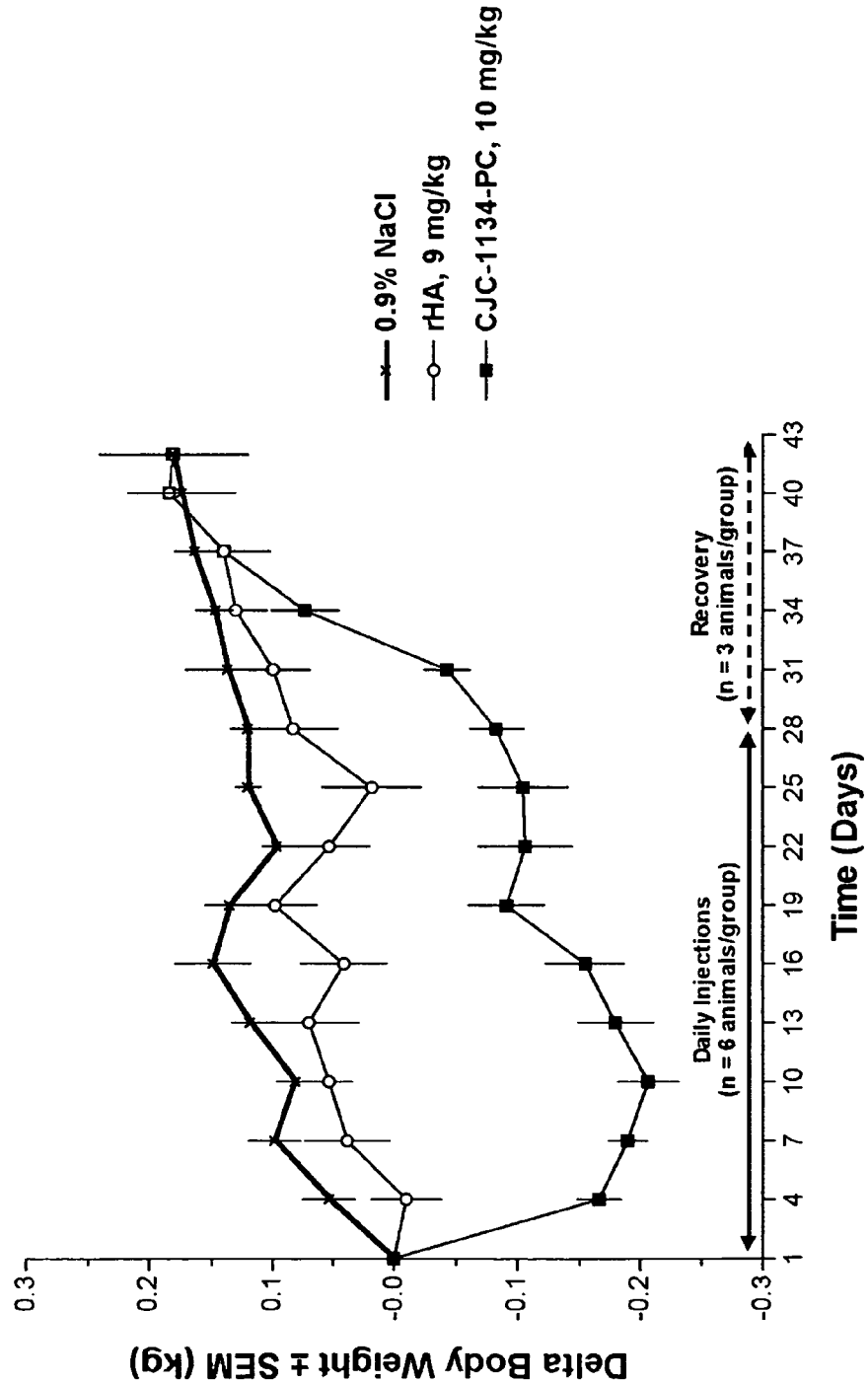
Figure 12:
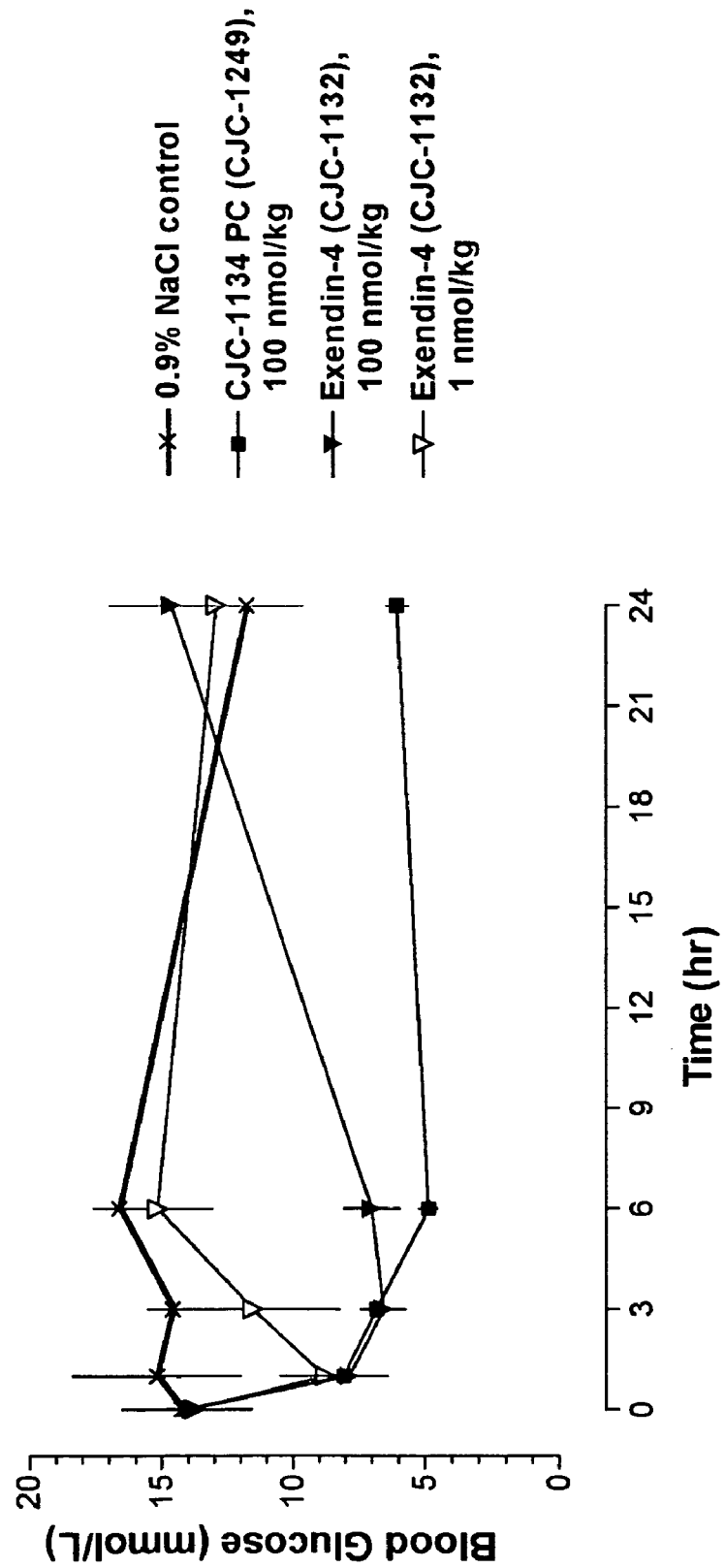
Figure 13:
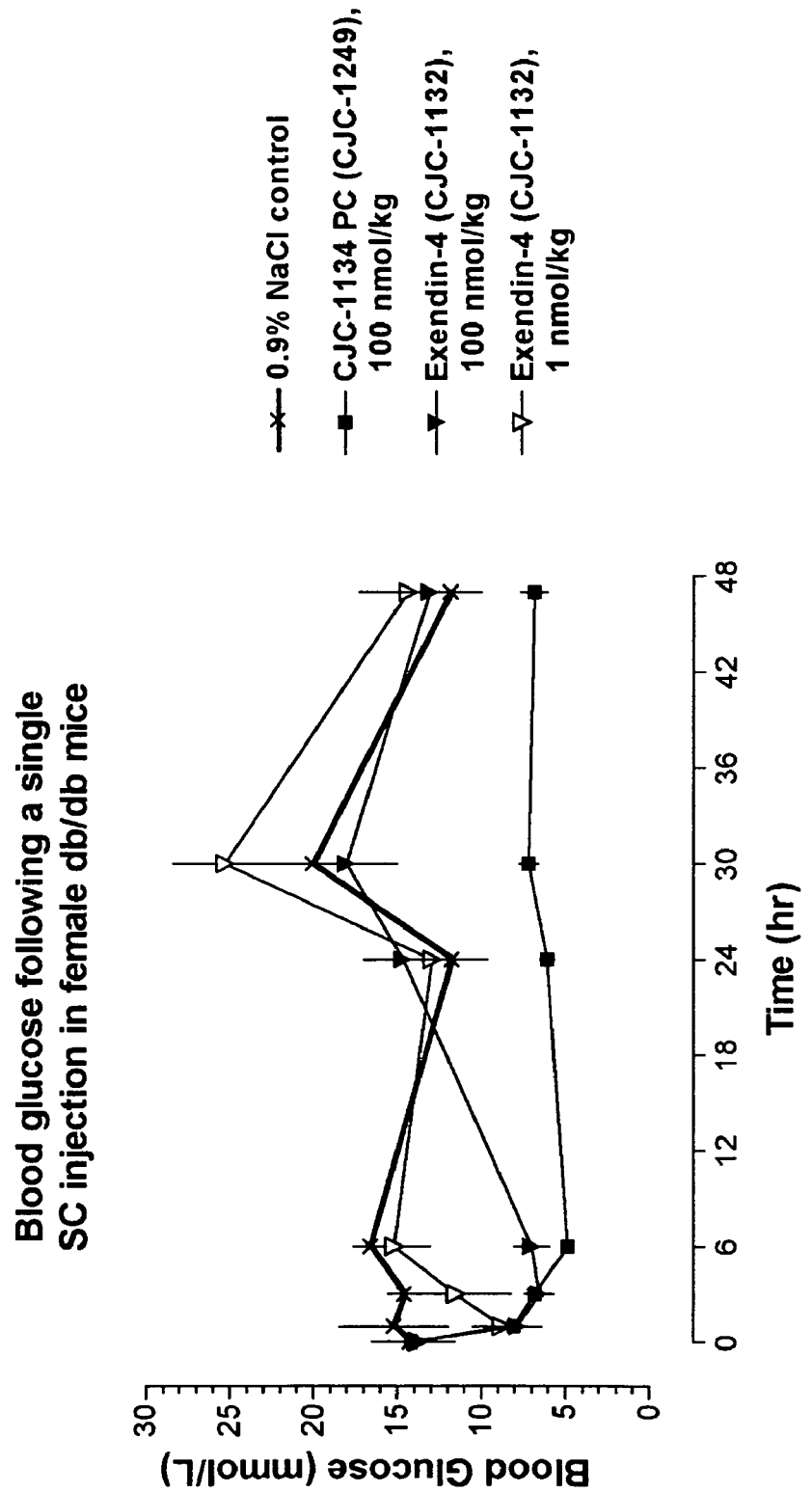
Figure 14:
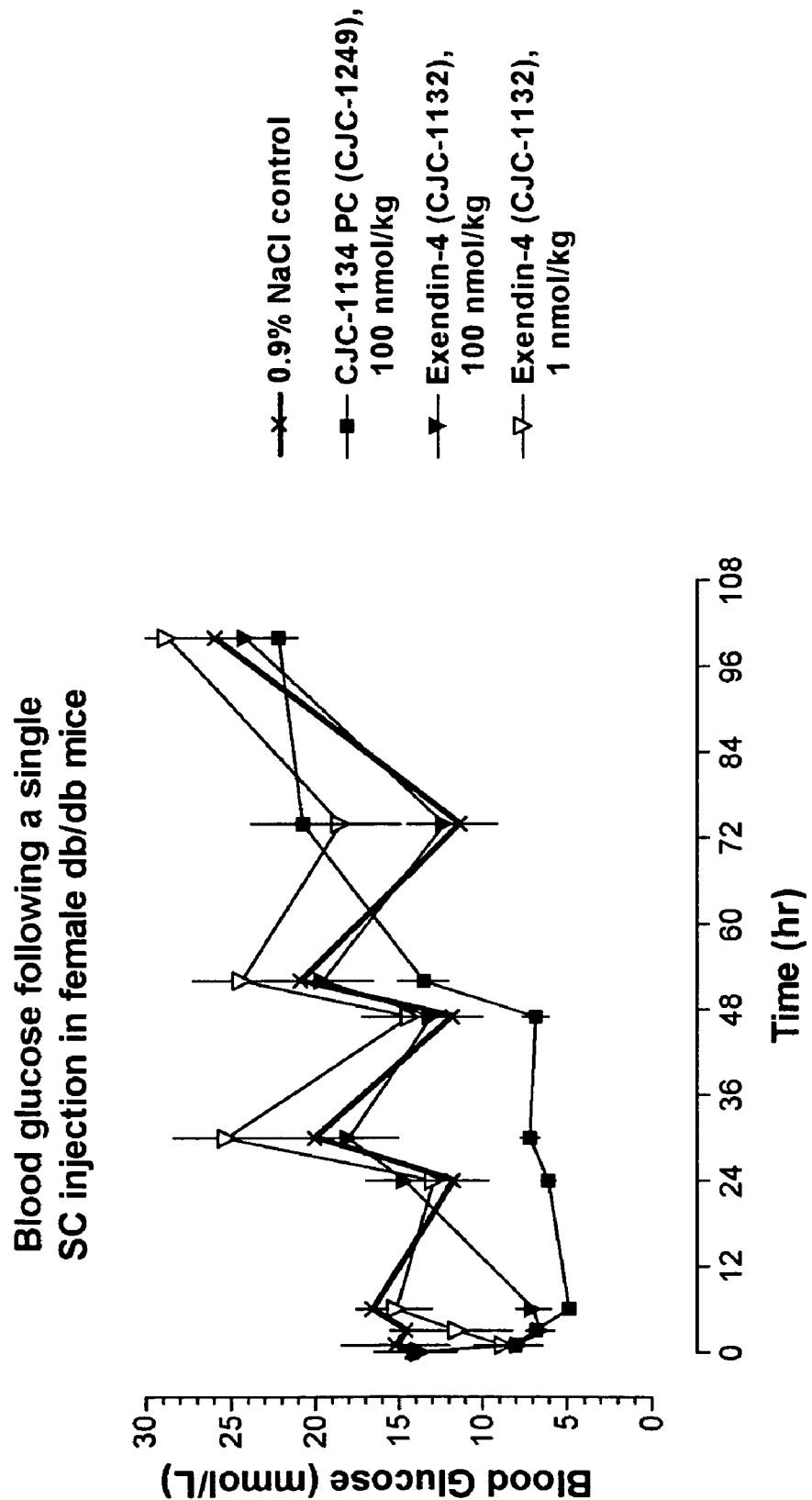
Figure 15:
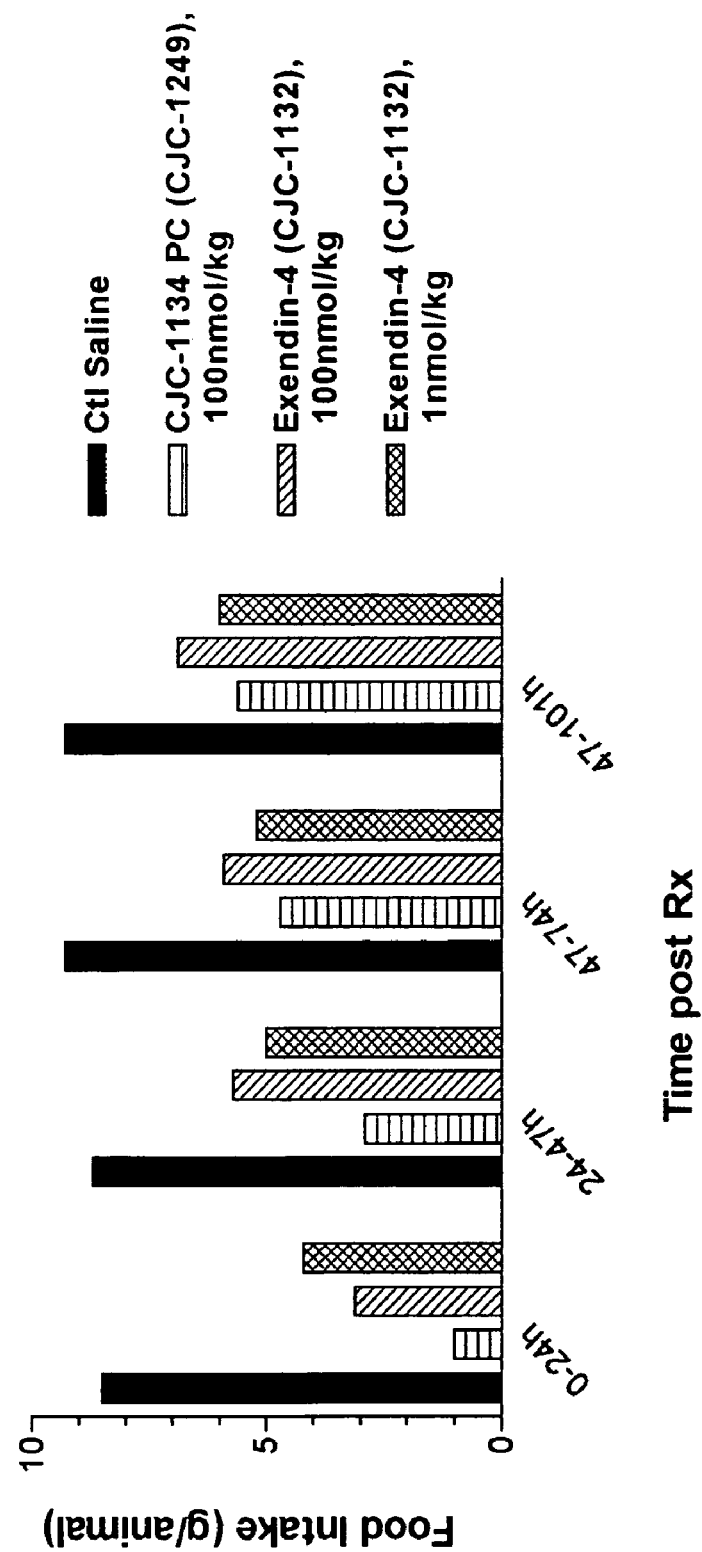
Figure 16:
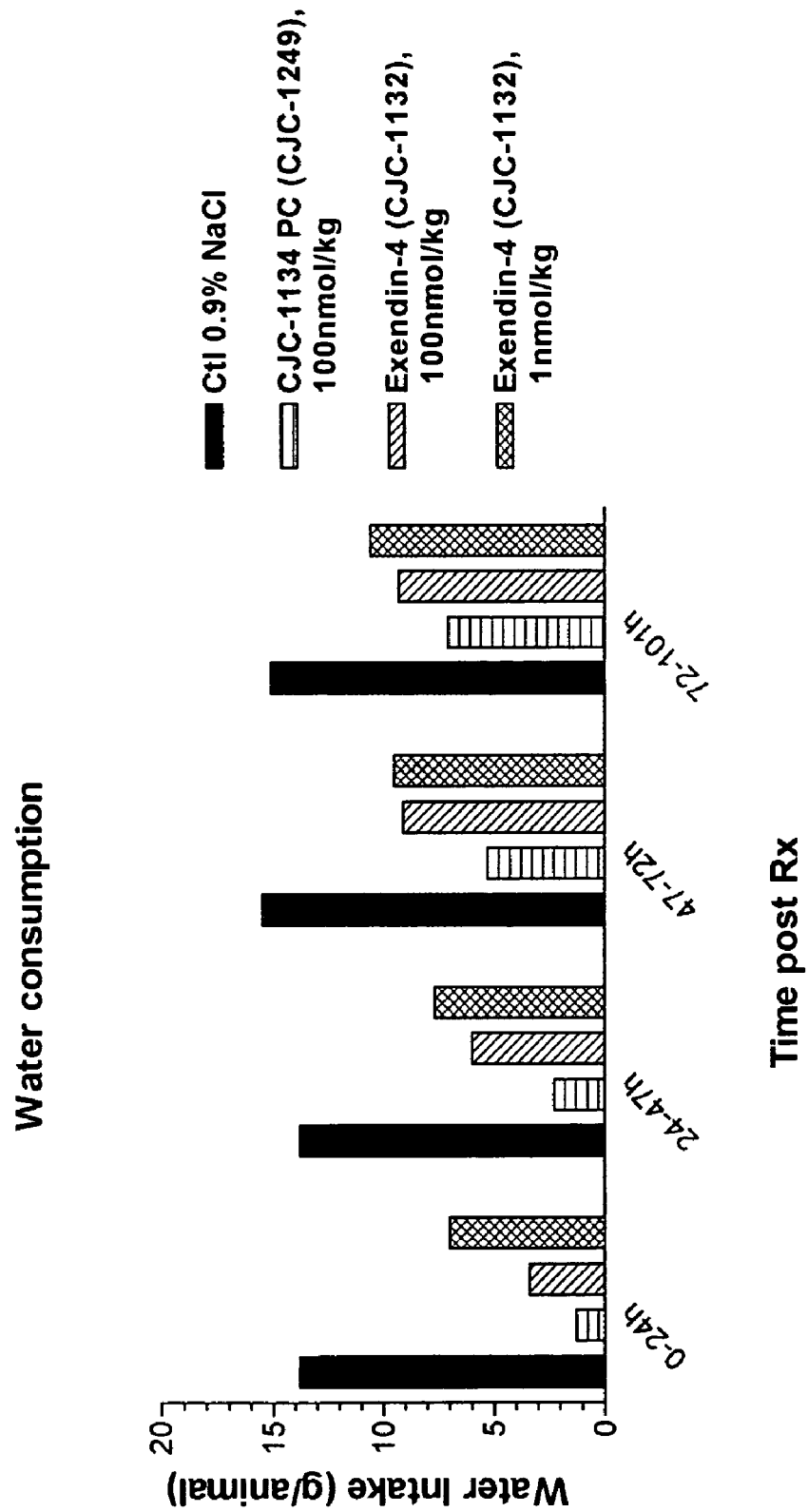
Figure 17:
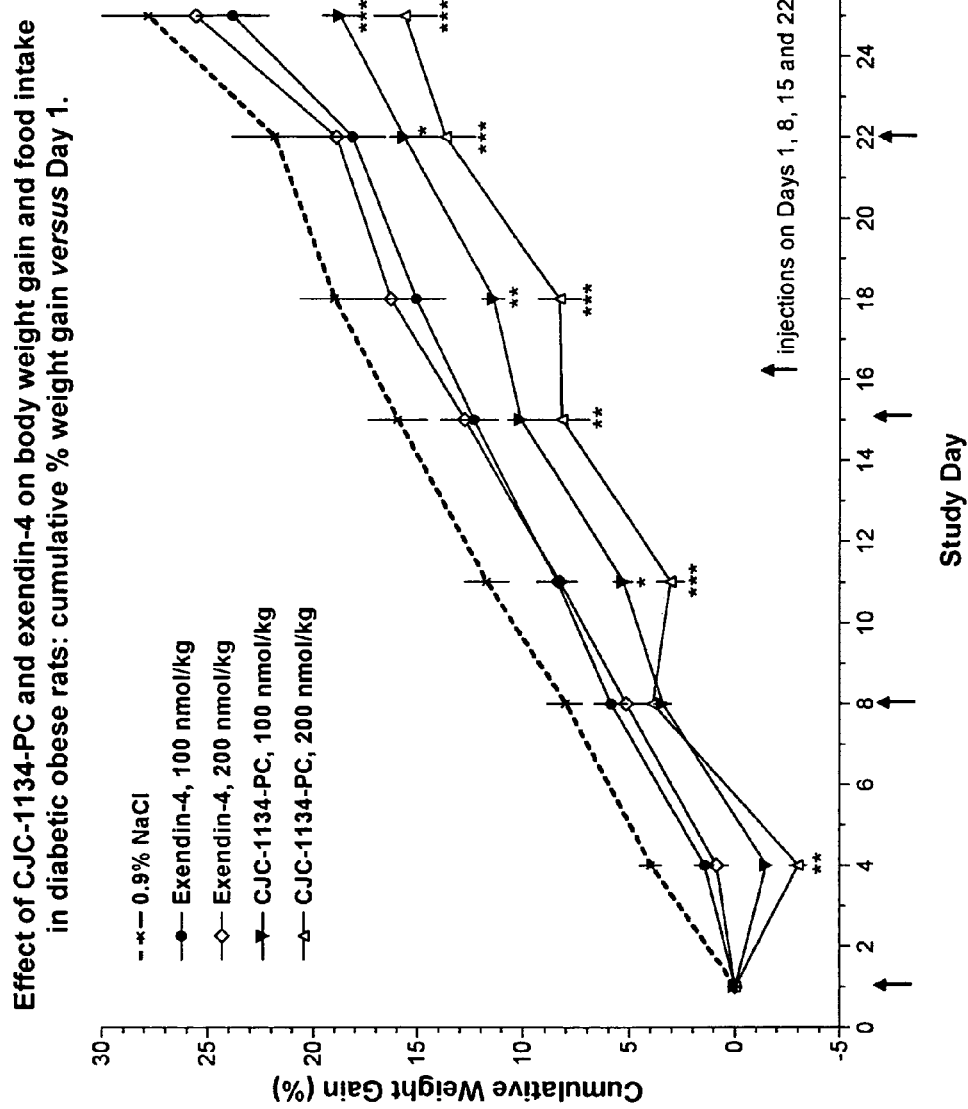
Figure 18:
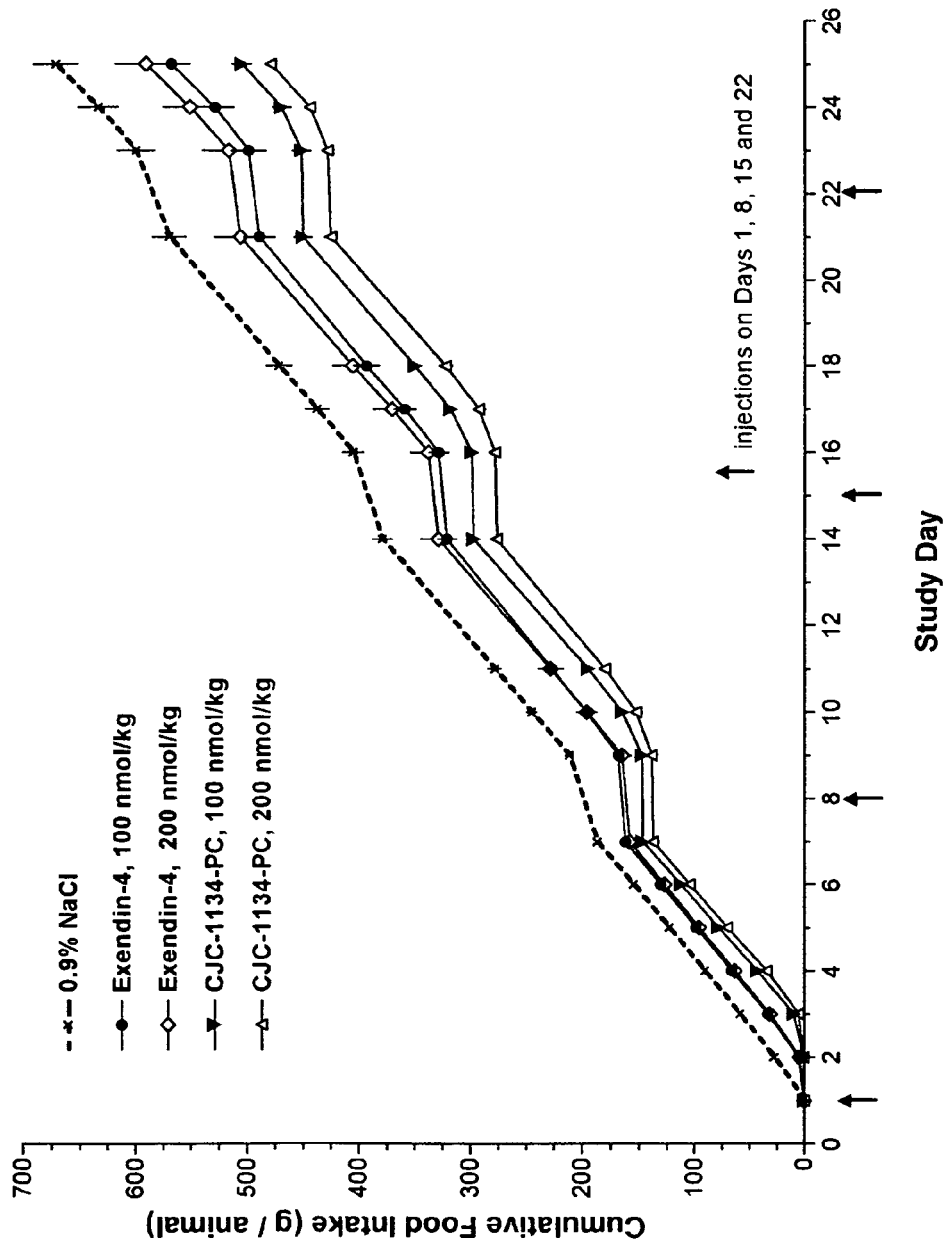

FIG. 1 presents a graph representing mean (±SEM) saccharin preference ratios in rats following intraperitoneal and subcutaneous administration of unconjugated exendin-4(1-39) versus exendin-4(1-39) Lys$^{40}$ ($\epsilon$-AEEA-MPA)-NH$_2$ conjugated with albumin (CJC-1134-PC), 72-84 hours post dose;

FIG. 2 presents a graph representing mean (±SEM) saccharin preference ratios in rats following intraperitoneal and subcutaneous administration of unconjugated exendin-4(1-39) versus CJC-1134-PC, 96-108 hours post dose;

FIG. 3 presents a graph representing mean cumulative kaolin intake (g/animal) in rats following administration of unconjugated exendin-4(1-39) versus CJC-1134-PC, 0-8 hours post dose;

FIG. 4 presents a graph representing mean (±SEM) food consumption (g/animal/day) over 7 days in rats following administration of CJC-1134-PC (0, 1, 5, and 25 mg/kg);

FIG. 5 presents a graph representing mean (±SEM) body weight (g) over 7 days in rats following administration of CJC-1134-PC (0, 1, 5, and 25 mg/kg);

FIG. 6 presents a graph representing mean (±SEM) food consumption (g/animal/day) over 28 days in rats (n=15) following administration of CJC-1134-PC (25 mg/kg) and over a two-week recovery (n=5);

FIG. 7 presents a graph representing delta (±SEM) body weight change (g) over 28 days in rats (n=15) following administration of CJC-1134-PC (25 mg/kg) and over a two week recovery (n=5);

FIG. 8 presents a graph representing delta (±SEM) food consumption (number of biscuits) over 7 days in monkeys following administration of CJC-1134-PC (0, 0.4, 2, and 10 mg/kg);

FIG. 9 presents a graph representing delta (±SEM) body weight change (kg) over 7 days in monkeys following administration of CJC-1134-PC (0, 0.4, 2, and 10 mg/kg);

FIG. 10 presents a graph representing mean (i SEM) food consumption (number of biscuits) over 28 days in monkeys (n=6) following administration of CJC-1134-PC (10 mg/kg) and over a two-week recovery (n=3);

FIG. 11 presents a graph representing delta (±SEM) body weight change (kg) over 28 days in monkeys (n=6) following administration of CJC-1134-PC (10 mg/kg) and over a two-week recovery (n=3);

FIG. 12 presents a graph representing blood glucose concentrations (nmol/L) over 24 hours in female db/db mice following a single subcutaneous administration of unconjugated exendin-4(1-39) versus CJC-1134-PC;

FIG. 13 presents a graph representing blood glucose concentrations (nmol/L) over 48 hours in female db/db mice following administration of unconjugated exendin-4(1-39) versus CJC-1134-PC;

FIG. 14 presents a graph representing blood glucose concentrations (nmol/L) over 101 hours in female db/db mice following administration of unconjugated exendin-4(1-39) versus CJC-1134-PC;

FIG. 15 presents a graph representing food consumption (g/animal) over 101 hours in female db/db mice following administration of unconjugated exendin-4(1-39) versus CJC-1134-PC;

FIG. 16 presents a graph representing water consumption (g/animal) over 101 hours in female db/db mice following administration of unconjugated exendin-4(1-39) versus CJC-1134-PC;

FIG. 17 presents a graph representing mean (±SEM) cumulative weight gain (%) over 25 days in male Zucker Diabetic Fatty (ZDF) rats following administration of unconjugated exendin-4(1-39) versus CJC-1134-PC; and FIG. 18 presents a graph representing mean (±SEM) cumulative food intake (g/animal) over 25 days in male ZDF rats following administration of unconjugated exendin-4(1-39) versus CJC-1134-PC.

5. DETAILED DESCRIPTION OF THE PREFERRED EMBODIMENTS

5.1 Definitions

As used herein, the following terms shall have the following meanings unless otherwise specified:

"Subject" refers to an animal such as a mammal, including but not limited to, a primate (e.g., human), cow, sheep, goat, horse, dog, cat, rabbit, rat, mouse and the like. In preferred embodiments, the subject is human. In certain embodiments, the subject is a non-human animal, for instance, a non-human animal such as a cow, sheep, goat, horse, dog, cat, rabbit, rat or mouse.

"Nausea" refers to any unpleasant sensation in the epigastrium, in the back of the throat, or in the abdomen. In some embodiments, nausea may culminate in vomiting. In some embodiments, nausea may not culminate in vomiting. In some embodiments, nausea can be sickness at the stomach, especially when accompanied by a loathing for food and an involuntary impulse to vomit. In some embodiments, nausea can be a feeling of sickness or discomfort in the stomach marked by an urge to vomit.

A "nausea-sensitive subject" is any subject who is prone to experiencing nausea in response to certain physical, chemical, and/or psychological stimuli. Exemplary stimuli are described herein. In some embodiments, the subject has a medical history of nausea sensitivity. In some embodiments, the subject has recently experienced nausea independent of administration of an insulinotropic peptide. In some embodiments, the subject has recently experienced nausea in response to administration of an insulinotropic peptide. In some embodiments, the subject is currently experiencing nausea independent of administration of an insulinotropic peptide. In some embodiments, the subject is currently experiencing nausea in response to administration of an insulinotropic peptide.

"Reducing," "reduces" or "reduced nausea side effect" refers to a reduction in the degree, duration, and/or frequency of nausea experienced by a subject following administration of an insulinotropic peptide conjugated to albumin compared to administration of an unconjugated insulinotropic peptide. Such reduction encompasses the prevention of nausea that a subject would otherwise experience in response to an unconjugated insulinotropic peptide. Such reduction also encompasses the elimination of nausea side effect previously experienced by a subject following administration of an unconjugated insulinotropic peptide. In some embodiments, "reducing" or "reduced nausea" encompasses a reduction of nausea wherein the nausea is reduced to zero or undetectable levels. In other embodiments, nausea is reduced but not completely eliminated.

As used herein, "compared to unconjugated insulinotropic peptide" is used interchangeably with "compared to insulinotropic peptide alone" and refers to amounts known to be comparable according to one of skill in the art. In some embodiments, the comparable amounts are equimolar amounts. In some embodiments, the comparable amounts are weight to weight equivalents.

"Insulinotropic peptide" refers to a peptide with insulinotropic activity. Insulinotropic peptides can stimulate, or cause the stimulation of, the synthesis or expression of the hormone insulin. Such peptides include precursors, derivatives, or fragments of peptides such as glucagon-like peptide, exendin-3 and exendin-4 and other peptides with insulinotropic activity.

"Glucagon-Like Peptide" ("GLP") and "GLP derivatives" are intestinal hormones which generally simulate insulin secretion during hyperglycemia, suppress glucagon secretion, stimulate (pro) insulin biosynthesis and decelerate gastric emptying and acid secretion. In some embodiments, the glucagon-like peptide is GLP-1(7-37). In some embodiments, the glucagon-like peptide is GLP-1(7-36). Some GLPs and GLP derivatives promote glucose uptake by cells but do not simulate insulin expression, as disclosed in U.S. Pat. No. 5,574,008 which is hereby incorporated by reference.

"Exendin-3" is a naturally occurring GLP-1 agonist isolated from salivary secretions of Heloderma horridum, the Mexican bearded lizard, and shares a 53% overlap with mammalian GLP-1 amino acid sequence, as disclosed in U.S. Pat. No. 5,424,286 which is hereby incorporated by reference.

"Exendin-4 is a naturally occurring GLP-1 agonist isolated from salivary gland venom of Heloderma suspectum, the Gila monster, and shares a 53% overlap with mammalian GLP-1 amino acid sequence as disclosed in U.S. Pat. No. 5,424,286 which is hereby incorporated by reference. Exendin-4 decreases glucagons and increases insulin secretion in a glucose-dependent manner, and mimics certain actions of GLP-1, including binding to and activating the human GLP-1 receptor. Exendin-4 improves glycemic control by reducing fasting and postprandial glucose concentrations through restoration of first-phase insulin response, regulation of glucagon secretion, delaying gastric emptying, and decreasing food intake.

"Reactive groups" are chemical groups capable of forming a covalent bond. Such reactive agents can be coupled or bonded to an insulinotropic peptide of interest to form a modified insulinotropic peptide. Reactive groups can generally be carboxy, phosphoryl, or convenient acyl group, either as an ester or a mixed anhydride, or an imidate, thereby capable of forming a covalent bond with functionalities such as an amino group, a hydroxy group or a thiol group at the target site on albumin. For the most part, the esters will involve phenolic compounds, or be thiol esters, alkyl esters, phosphate esters, or the like. Reactive groups include succinimidyl-containing groups and maleimido-containing groups.

"Functionalities" are groups on albumin to which reactive groups on modified insulinotropic peptides are capable of reacting with to form covalent bonds. Functionalities include hydroxyl groups for bonding to ester reactive entities; thiol groups for bonding to maleimides and maleimido-containing groups, imidates and thioester groups; and amino groups for bonding to carboxy groups, phosphoryl groups, acyl groups, succinimidyl-containing groups or maleimido-containing groups on reactive entities.

"Linking Groups" are chemical moieties capable of connecting reactive groups to insulinotropic peptides. Linking groups may comprise one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heterocyclic groups, and substituted heterocyclic groups. Linking groups may also comprise poly ethoxy aminoacids such as AEA ((2-amino) ethoxy acetic acid) or a preferred linking group AEEA ([2-(2-amino)ethoxy)]ethoxy acetic acid). In certain embodiments, a linking group can comprise, for example, a chain of 0-30 atoms, or 0-20 atoms, or 0-10 atoms. In certain embodiments, a linking group can consist of, for example, a chain of 0-30 atoms, or 0-20 atoms, or 0-10 atoms. Those atoms can be selected from the group consisting of, for example, C, N, O, S, P.

As used herein, "albumin" refers to the most abundant protein in blood plasma having a molecular weight of approximately between 65 and 67 kilodaltons in its monomeric form, depending on the species of origin. The term "albumin" is used interchangeably with "serum albumin" and is not meant to define the source of the albumin which forms a conjugate with the modified peptides of the invention. Thus, the term "albumin" as used herein may refer either to albumin purified from a natural source such as blood or serous fluids, or it may refer to chemically synthesized or recombinantly produced albumin.

A "conjugated insulinotropic peptide" is an insulinotropic peptide that has been conjugated to macromolecule, for example albumin, via a covalent bond formed between the insulinotropic peptide and a functionality on the macromolecule. In some embodiments, the insulinotropic peptide has been modified to contain a reactive group to which the macromolecule is covalently bound. In some embodiments, the reactive group is coupled to the insulinotropic peptide via a linking group.

"Preventing" or "prevention" of any disease or disorder refers to a reduction in the risk of acquiring a disease or disorder (i.e., causing at least one of the clinical symptoms of the disease not to develop in a subject that may be exposed or predisposed to the disease but does not yet experience or display symptoms of the disease). Preferably, prevention refers to the use of a compound or composition in a subject not yet affected by the disease or disorder or not yet exhibiting a symptom of the disease or disorder, for instance a subject not yet infected or not yet exhibiting the symptoms of infection.

"Treating" or "treatment" of any disease or disorder refers, in one embodiment, to ameliorating the disease or disorder (i.e., arresting or reducing the development of the disease or at least one of the clinical symptoms thereof) that exists in a subject. In another embodiment, "treating" or "treatment" refers to ameliorating at least one physical parameter, which may be indiscernible by the subject. In yet another embodiment, "treating or treatment" refers to modulating the disease, either physically (e.g., stabilization of a discernable symptom) or physiologically (e.g., stabilization of a physical parameter) or both. In yet another embodiment, "treating" or "treatment" refers to delaying the inset of the disease or disorder.

Effective amount: "an effective amount" means an amount of a conjugated insulinotropic peptide that when, administered to a subject for treating a disease is sufficient to effect such treatment for the disease. An effective amount can vary depending on, inter alia, the insulinotropic peptide used, the disease and its severity and the age, weight, etc. of the subject to be tested. In certain embodiments, the amount is effective to treat diabetes or obesity. In certain embodiments, the amount is effective to treat type 1 diabetes or type 2 diabetes. In certain embodiments, the amount is effective to lower blood glucose, to lower whole blood glucose, to lower plasma blood glucose and/or to lower HbA1c levels. In certain embodiments, the levels can be lowered by 5%, 10%, 15% or more. In certain embodiments, the levels on average can be lowered for at least one day, at least two days, at least three days, at least four days or least one week.

5.2 Methods of Treatment with Reduced Nausea

Although not intending to be bound by any particular theory of operation, the present invention is based, in part, on the discovery that certain populations of subjects receiving insulinotropic peptides for the treatment of a disorder or condition experience nausea side effect in response to the administration of the insulinotropic peptide. It is further discovered that administration to a subject of an insulinotropic peptide conjugated to albumin can reduce nausea side effect compared to administration of the insulinotropic peptide alone.

Accordingly, the present invention provides methods of treating a disorder or condition with a form of insulinotropic peptide that provides reduced nausea. The methods comprise the step of administering to the subject an amount of an insulinotropic peptide conjugated to albumin effective to treat the disorder or condition with reduced nausea side effect.

Exemplary disorders or conditions treatable with an insulinotropic peptide include, but are not limited to, obesity and diabetes, including maturity onset diabetes mellitus (type II diabetes). In certain embodiments, the disorder or condition treatable with an insulinotropic peptide is obesity. In another embodiment, the disorder or condition treatable with an insulinotropic peptide is diabetes. In certain embodiments, the disorder or condition treatable with an insulinotropic peptide is type II diabetes.

Nausea of the present invention can be any unpleasant sensation in the epigastrium, in the back of the throat, or in the abdomen. In some embodiments, nausea may culminate in vomiting. In some embodiments, nausea may not culminate in vomiting. In some embodiments, nausea can be sickness at the stomach, especially when accompanied by a loathing for food and an involuntary impulse to vomit. In some embodiments, nausea can be a feeling of sickness or discomfort in the stomach marked by an urge to vomit. In some embodiments, the nausea is mild. In some embodiments, the nausea is moderate. In some embodiments, the nausea is severe. In some embodiments the nausea does not interfere with the normal daily life of the subject. In some embodiments the nausea interferes with normal daily life. In some embodiments the subject is bedridden because of the nausea.

In one aspect, the present invention provides methods of preventing nausea in a subject in response to the administration of an insulinotropic peptide. In another aspect, the present invention provides methods of reducing nausea in a subject in response to the administration of an insulinotropic peptide. In another aspect, the present invention provides methods of eliminating nausea in a subject in response to the administration of an insulinotropic peptide.

It should be recognized that the methods of the invention encompass the prevention, reduction, and elimination of nausea in a subject receiving an insulinotropic peptide for the treatment of a disorder or condition by selecting patients who are prone to experiencing, have experienced, or are experiencing nausea. Those more likely to benefit from reduced nausea are identified by determining their nausea sensitivity either resulting from, or arising independent of, the administration of an unconjugated insulinotropic peptide.

5.2.1 Subjects

In certain embodiments of the invention, the subject is an animal, preferably a mammal, more preferably a non-human primate. In certain embodiments, the subject is a human patient. The subject can be a male or female subject. In certain embodiments, the subject is a non-human animal, such as, for instance, a cow, sheep, goat, horse, dog, cat, rabbit, rat or mouse.

The methods of the invention can be used for selecting a subject for treatment with an insulinotropic peptide conjugated to albumin. Particularly useful subjects include those that have a disorder or condition treatable with an insulinotropic peptide that are prone to experiencing, have experienced, or are experiencing nausea.

In certain embodiments, the subject is at risk for a disorder or a condition treatable with an insulinotropic peptide including, but not limited to, obesity and type II diabetes. In some embodiments the subject is at risk for obesity. In some embodiments the subject is at risk for type II diabetes.

In some embodiments, the subject is not healthy. In some embodiments the subject has or suffers from a condition treatable with an insulinotropic peptide including, but not limited to, obesity or type II diabetes.

In some embodiments, the subject is obese. In some embodiments, the subject is a human and has a Body Mass Index (BMI) of 30 kg/m$^2$ or greater. In some embodiments, the subject is a human and has a BMI between 30 kg/m$^2$ and 35 kg/m$^2$. In some embodiments, the subject is a human and has a BMI of 35 kg/m$^2$ or greater. In some embodiments, the subject is a human and has a BMI of 40 kg/m$^2$ or greater. In some embodiments, the subject weighs more than 120% of the normal weight for its age and height. In some embodiments, the subject is a human and weighs more than 96 kg.

In some embodiments, the subject has type II diabetes. In some embodiments, the subject has abnormal glucose levels. In particular embodiments, the subject has a high glucose level. In some embodiments, the subject is a human and has an average whole blood glucose level of 8 mmol/L (138 mg/dl) or greater, and an average plasma blood glucose level of 9.0 mmol/L (154 mg/dl) or greater. In some embodiments, the subject is a human and has an average whole blood glucose level between 8 mmol/L (138 mg/dl) and 16 mmol/L (281 mg/dl), and an average plasma blood glucose level between 9.0 mmol/L (154 mg/dl) and 17 mmol/L (314 mg/dl). In some embodiments, the subject is a human and has an average whole blood glucose level greater than 16 mmol/L (281 mg/dl), and an average plasma blood glucose level greater than 17 mmol/L (314 mg/dl).

In some embodiments, the subject is a human and has a glycosylated hemoglobin (HbA1c) level of 6.5% or greater. In some embodiments, the subject is a human and has a HbA1c level between 6.5% and 11%. In some embodiments, the subject is human and has a HbA1c level of 11% or greater.

5.2.2 Assessing Nausea in Subjects Having a Disorder or Condition Treatable with an Insulinotropic Peptide Whether a subject is prone to experiencing, has experienced, or is experiencing nausea can be determined according to any technique known to those of skill in the art without limitation. In certain embodiments, the technique for assessing nausea is not critical for the invention. In certain embodiments, the assessment of nausea is determined according to the judgment of the practitioner in the art. In certain embodiments, the assessment of nausea is determined by the subjective experience of the subject. In certain embodiments nausea is determined by the subjective experience of the subject combined with objective elements such as pallor, sweating and feeling cold.

In some embodiments the assessment of nausea is determined according to the Duke Descriptive Scale (DDS). See Laszlo et al., 1981, *J. Clin. Phamacol.* 2:51S-56S; Cotanch, 1983, *Cancer Nurs.* 6:277-283; the entirety of which are incorporated by reference herein. The DDS grades nausea on a scale of I to IV, taking into account intensity, severity, and impairment in patient activity for a 24-hour period. In grade I, the subject has experienced no nausea. In grade II, the nausea is mild, with no interference in daily activities. In grade III, the nausea is moderate, with some interference in daily activities. In grade IV, the nausea is severe, and the subject is bedridden with nausea for more than 2 hours.

In some embodiments the assessment of nausea is determined according to the Visual Analog Scale (VAS). See Bennett et al., 1989, *Oncol. Nurs. Forum* 16:175, the entirety of which is incorporated by reference herein. The VAS is a line, usually 100 mm in length, occasionally 150 or 160 mm long, with anchors at each end to indicate the extremes of the nausea experienced by the subject. The low endpoint is to the left in a horizontally oriented scale, and at the base of a vertically oriented scale. Subjects indicate the point on the scale corresponding to the degree of nausea they are experiencing. Investigators score the intensity of the discomfort by measuring the millimeters from the low end of the scale to the mark.

In some embodiments the assessment of nausea is determined according to the Rhodes Index of Nausea and Vomiting (INV). See Rhodes et al., 1994, *Cancer Nurs.* 17:45-51; Rhodes et al., 1986, *Oncol. Nurs. Forum* 13:41-47; Rhodes et al., 1988, *Appl. Nurs. Res.* 1:143-144; the entireties of each of which are incorporated by reference herein. The NV measures the individual components of nausea, vomiting, retching, and associated distress. This 8-item, 5-point scale measures a subject's perceived (1) duration of nausea; (2) frequency of nausea; (3) distress from nausea; (4) frequency of vomiting; (5) amount of vomiting; (6) distress from vomiting; and (7) frequency of retching. An exemplary INV item is: "During the last 12 hours, I have not felt any distress from nausea/sickness at my stomach"; "During the last 12 hours I have felt mild distress from nausea or sickness at my stomach"; "During the last 12 hours I have felt moderate distress from nausea or sickness at my stomach"; "During the last 12 hours I have felt great distress from nausea or sickness at my stomach"; "During the last 12 hours I have felt as severe distress from nausea or sickness at my stomach as can be."

In some embodiments the assessment of nausea is determined according to the Functional Living Index-Emesis (FLIE). See Lindley et al., 1992, *Qual. Life Res.* 1:331-340, the entirety of which is incorporated by reference herein. The FLIE is a self-administered questionnaire which focuses on the effects of nausea and vomiting on physical activities, social and emotional function, and the ability to enjoy food. An exemplary FLIE item is: "How much nausea have you had in the past 3 says?" Each item is answered in a range from 1 to 7, with 9 items for nausea and 9 items for vomiting. A total score is created by adding the responses to the 18 questions. The range of total scores possible is between 18 (all 1 responses on the scale) and 126 (all 7 responses on the scale). Lower scores indicate a more negative impact of nausea and vomiting; higher scores indicate a higher impact.

In some embodiments the assessment of nausea is determined according to a daily diary of the subject. See Baltzer et al., 1994, *Cancer* 73:720-723; Buser et al., 1993, *Ann. Oncol.* 4:475479; Sung et al., 1993, *J. Clin. Anesthes.* 5:22-29; the entireties of each of which are incorporated by reference herein. Diaries have been used for periods ranging from 24 hours to 15 days. This method requires subject self-report and has been correlated to other measures such as observation and the FLIE.

5.2.3 Selecting Subjects for Treatment with a Conjugated Insulinotropic Peptide

Subjects having a disorder or condition treatable with an insulinotropic peptide are selected for treatment with an insulinotropic peptide conjugated to albumin if they are prone to experiencing, have experienced, or are experiencing nausea. Whether a subject is prone to experiencing, has experienced, or is experiencing nausea can be determined according to the judgment of the practitioner of the art. Exemplary methods are described herein.

In some embodiments, nausea of the present invention can be of any degree, duration, or frequency experienced by the subject as determined by the practitioner of the art. In some embodiments, nausea can be of any degree, duration, or frequency as determined by the subjective experience of the subject. In some embodiments, nausea can be of any degree, duration, or frequency according to the DDS. In some embodiments, nausea can be of any degree, duration, or frequency according to the VAS. In some embodiments, nausea can be of any degree, duration, or frequency according to the INV. In some embodiments, nausea can be of any degree, duration, or frequency according to the FLIE. In some embodiments, nausea can be of any degree, duration, or frequency according to a daily diary of the subject.

In certain embodiments, subjects who are prone to experiencing nausea are selected for treatment. In some embodiments, the subject has a medical history of nausea sensitivity independent of the administration of an unconjugated insulinotropic peptide. A subject who is prone to experiencing nausea may experience nausea due to any cause known in the art. For example, a subject prone to nausea may experience nausea in response to any physical, chemical, and/or psychological stimuli.

Exemplary stimuli include, but are not limited to: psychological problems, including anxiety, stress and depression; severe pain or shock; unpleasant smells or pictures; disturbances in the inner ear in conditions such as altitude sickness; Meniere's disease; motion sickness and labyrinthitis; diseases of the internal organs (viscera); gastrointestinal disease such as gastritis, peptic ulcer, stomach cancer, gut obstruction, appendicitis and mesenteric adenitis; disease of the liver or gallbladder such as cholecystitis, hepatitis and cirrhosis; pancreatitis; disease of the heart such as myocarditis, severe hypertension, heart attack (myocardial infarction) and congestive heart failure; disease of the brain such as migraine, stroke (cerebrovascular accident), brain tumors, cerebral hypoxia, and epilepsy; diseases of the urinary tract such as urinary tract infections and renal colic; chemicals and toxins; bacterial and viral infections, such as cholera and salmonella, that can cause either gastro-intestinal or systemic infections; parasitic infections, such as malaria; meningitis; sinusitis; endocrine problems, such as hyperparathyroidism, hyperthyroidism and diabetes mellitus; waste products that accumulate in the body with renal failure, and other electrolyte disturbances; certain drugs and hormones including digoxin, morphine, codeine, estrogens, iron preparation and aminophylline; morning sickness; haemolytic anaemia; porphyria; alcoholism; radiotherapy; self-induced vomiting in psychiatric conditions such as bulimia nervosa; congenital malformations of the gastro-intestinal tract such as pyloric stenosis and gastro-oesophageal reflux; and constipation.

In some embodiments, subjects who have recently experienced nausea are selected for treatment. In some embodiments, the nausea was experienced independent of administration of an unconjugated insulinotropic peptide. In other embodiments, the nausea was experienced as a result of a single administration of an unconjugated insulinotropic peptide. In other embodiments, the nausea was experienced as a result of more than one administration of an unconjugated insulinotropic peptide.

In some embodiments, the subject experienced acute nausea as a result of administration of the unconjugated insulinotropic peptide. In some embodiments, the nausea was experienced within 23, 22, 21, 20, 19, 18, 17, 16, 15, 14, 13, 12, 11, 10, 9, 8, 7, 6, 5, 4, 3, 2 or 1 hour(s) of a single administration of the unconjugated insulinotropic peptide. In some embodiments, the nausea was experienced within 23, 22, 21, 20, 19, 18, 17, 16, 15, 14, 13, 12, 11, 10, 9, 8, 7, 6, 5, 4, 3, 2 or 1 hour(s) of more than one administration of the unconjugated insulinotropic peptide.

In other embodiments, the subject experienced delayed nausea as a result of administration of the unconjugated insulinotropic peptide. In some embodiments, the nausea was experienced within 10, 9, 8, 7, 6, 5, 4, 3, 2, or 1 day(s) of a single administration of the unconjugated insulinotropic peptide. In some embodiments, the nausea was experienced within 10, 9, 8, 7, 6, 5, 4, 3, 2, or 1 day(s) of more than one administration of the unconjugated insulinotropic peptide.

In some embodiments, subjects who are currently experiencing nausea are selected for treatment. In some embodiments, the subject is experiencing nausea independent of administration of an unconjugated insulinotropic peptide. In other embodiments, the subject is experiencing nausea as a result of a single administration of an unconjugated insulinotropic peptide. In other embodiments, the subject is experiencing nausea as a result of more than one administration of an unconjugated insulinotropic peptide.

In some embodiments, the subject is experiencing acute nausea as a result of administration of the unconjugated insulinotropic peptide. In some embodiments, the subject is experiencing nausea within 23, 22, 21, 20, 19, 18, 17, 16, 15, 14, 13, 12, 11, 10, 9, 8, 7, 6, 5, 4, 3, 2 or 1 hour(s) of a single administration of an unconjugated insulinotropic peptide. In some embodiments, the subject is experiencing nausea within 23, 22, 21, 20, 19, 18, 17, 16, 15, 14, 13, 12, 11, 10, 9, 8, 7, 6, 5, 4, 3, 2 or 1 hour(s) of more than one administration of an unconjugated insulinotropic peptide.

In other embodiments, the subject is experiencing delayed nausea as a result of administration of the unconjugated insulinotropic peptide. In some embodiments, the subject is experiencing nausea within 10, 9, 8, 7, 6, 5, 4, 3, 2, or 1 day(s) of a single administration of an unconjugated insulinotropic peptide. In some embodiments, the subject is experiencing nausea within 10, 9, 8, 7, 6, 5, 4, 3, 2, or 1 day(s) of more than one administration of an unconjugated insulinotropic peptide.

In some embodiments, subjects are selected for treatment with a conjugated insulinotropic peptide of the present invention after a first instance of nausea in response to administration of an unconjugated insulinotropic peptide. In some embodiments, subjects are selected for treatment with a conjugated insulinotropic peptide after more than one instance of nausea in response to administration of an unconjugated insulinotropic peptide.

In addition to the assessment of nausea, other parameters or variables can be used in combination with the assessment of nausea to select a subject for treatment with an insulinotropic peptide conjugated to a macromolecule, for example albumin. In some embodiments, average whole blood glucose levels of the subject are used. In some embodiments, average plasma blood glucose levels of the subject are used. In some embodiments, HbA1c levels of the subject are used. In other embodiments, the body weight or BMI of the subject is used to make the selection.

5.2.4 Administration of the Conjugated Insulinotropic Peptide

The conjugated insulinotropic peptide can be administered according to any technique deemed suitable by one of skill in the art. In some embodiments, the conjugated insulinotropic peptides can be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 4.0 to 8.0, preferably in the range of about 5.0 to 8.0 and more preferably in the range of about 5.0 to 7.2, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The conjugated insulinotropic peptides can for the most part be administered orally, parenterally, such as intravascularly (IV), intraarterially (IA), intramuscularly (IM), subcutaneously (SC), rectally, intradermally, intranasally, by inhalation or the like. Administration may in appropriate situations be by transfusion. Usually a single injection will be employed although more than one injection may be used, if desired. The conjugated insulinotropic peptides may be administered by any convenient means, including pen, needle-free device, enema, suppository, patch, inhaler, metered dose inhaler, syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Also preferably, the administration will be subcutaneously.

5.2.5 Dosage and Frequency of Administration

The dosage and frequency of administration of the conjugated insulinotropic peptide will be determined according to one of ordinary skill in the art. The amount of a conjugated insulinotropic peptide in the methods of the invention which will be effective in the treatment of a disorder or condition with reduced nausea will vary with the nature and severity of the disorder or condition, and the route by which the active ingredient is administered. The frequency and dosage will also vary according to factors specific for each patient depending on the severity of the disorder or condition, the route of administration, as well as age, body weight, response, and the past medical history of the patient. Effective doses may be extrapolated from dose-response curves derived from in vitro or animal model test systems.

Exemplary doses of a conjugated insulinotropic peptide include milligram or microgram amounts of the conjugated insulinotropic peptide per kilogram of subject or sample weight (e.g., about 1 mg to about 10 mg per dose, for example 1 mg, 3 mg, 5 mg or 10 mg per dose).

In some embodiments, the conjugated insulinotropic peptide can be administered as, for example, a single dose, a once-a-day dose, a once-a-week dose, a once-every-two weeks dose, a once-every-three-weeks dose or a once-a-month dose. In some embodiments, the weekly dose is administered once a week and the dose comprises the conjugated insulinotropic peptide in an amount between about 1000 to 4000 µg, preferably about 1250 to 3750 µg, and especially about 1250 to 2500 µg. Exemplary doses include 1000 µg, 1250 µg, 2500 µg and 3750 µg.

In certain aspects, the present invention provides unit dosages comprising a conjugated insulinotropic peptide, or a pharmaceutically acceptable salt thereof, in a form suitable for administration. Such forms are described in detail above. In certain embodiments, the unit dosage comprises 1000 to 4000 µg, 1250 to 3750 µg or 1250 to 2500 µg active ingredient. In particular embodiments, the unit dosages comprise about 1000, 1250, 1500, 1750, 2000, 2250, 2500, 2750, 3000, 3250, 3500, 3750 or 4000 µg active ingredient. Such unit dosages can be prepared according to techniques familiar to those of skill in the art.

Different therapeutically effective amounts of the conjugated insulinotropic peptide may be applicable for different disorders and conditions, as will be readily known by those of ordinary skill in the art. Similarly, amounts sufficient to prevent, mange, treat or ameliorate such disorders or conditions, but still sufficient to reduce nausea relative to administration of an unconjugated insulinotropic peptide are also encompassed by the above described dosage amounts and dose frequency schedules.

In certain embodiments, the methods and compositions can be practiced as a single, one time dose or chronically. By chronic it is meant that the methods and compositions of the invention are practiced more than once to a given individual. For example, chronic administration can be multiple doses of a pharmaceutical composition administered to a subject, on a weekly basis, monthly basis, or more or less frequently, as will be apparent to those of skill in the art. Chronic administration can continue for weeks, months, or years if appropriate according to the judgment of the practitioner of skill.

An effective amount of a conjugated insulinotropic peptide described herein will provide therapeutic benefit with reduced nausea without causing substantial toxicity.

Toxicity of a conjugated insulinotropic peptide can be determined by standard pharmaceutical procedures in cell cultures or experimental animals, for example, by determining the LD 50 (the dose lethal to 50% of the population) or the LD 100 (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1996, In: The Pharmacological Basis of Therapeutics, 9th ed., Chapter 2, p. 29, Elliot M. Ross).

5.3 Insulinotropic Peptides

Useful insulinotropic peptides include GLP-1, exendin-3 and exendin-4, and their precursors, derivatives and fragments. Such insulinotropic peptides include those disclosed in U.S. Pat. Nos. 6,514,500; 6,821,949; 6,887,849; 6,849,714; 6,329,336; 6,924,264; WO 03/103572 and 6,593,295, each of which are hereby incorporated by reference in their entirety.

In some embodiments, the insulinotropic peptide is GLP-1. In some embodiments, the insulinotropic peptide is a GLP-1 derivative. In some embodiments, the insulinotropic peptide is exendin-3. In some embodiments, the insulinotropic peptide is an exendin-3 derivative. In some embodiments, the insulinotropic peptide is exendin-4. In some embodiments, the insulinotropic peptide is an exendin-4 derivative. In some embodiments, the insulinotropic peptide is exendin-4(1-39). In some embodiments, the insulinotropic peptide is exendin-4(1-39)Lys$^{40}$.

5.3.1 GLP-1 and Its Derivatives

The hormone glucagon can be synthesized according to any method known to those of skill in the art. In some embodiments, it is synthesized as a high molecular weight precursor molecule which is subsequently proteolytically cleaved into three peptides: glucagon, GLP-1, and glucagon-like peptide 2 (GLP-2). GLP-1 has 37 amino acids in its unprocessed form as shown in SEQ ID NO: 1 (HDEFERHAEG TFTSDVSSYL EGQAAKEFIA WLVKGRG). Unprocessed GLP-1 is essentially unable to mediate the induction of insulin biosynthesis. The unprocessed GLP-1 peptide is, however, naturally converted to a 31-amino acid long peptide (7-37 peptide) having amino acids 7-37 of GLP-1 ("GLP-1(7-37)") SEQ ID NO:2 (HAEG TFTSDVSSYL EGQAAKEFIA WLVKGRG). GLP-1(7-37) can also undergo additional processing by proteolytic removal of the C-terminal glycine to produce GLP-1(7-36) which also exists predominantly with the C-terminal residue, arginine, in amidated form as arginineamide, GLP-1(7-36) amide. This processing occurs in the intestine and to a much lesser extent in the pancreas, and results in a polypeptide with the insulinotropic activity of GLP-1(7-37).

A compound is said to have an "insulinotropic activity" if it is able to stimulate, or cause the stimulation of, the synthesis or expression of the hormone insulin. The hormonal activity of GLP-1(7-37) and GLP-1(7-36) appear to be specific for the pancreatic beta cells where it appears to induce the biosynthesis of insulin. Glucagon-like-peptide hormones are useful in the study of the pathogenesis of maturity onset diabetes mellitus, a condition characterized by hyperglycemia in which the dynamics of insulin secretion are abnormal. Moreover, glucagon-like peptides are useful in the therapy and treatment of this disease, and in the therapy and treatment of hyperglycemia.

Peptide moieties (fragments) can be chosen from the determined amino acid sequence of human GLP-1. The interchangeable terms "peptide fragment" and "peptide moiety" are meant to include both synthetic and naturally occurring amino acid sequences derivable from a naturally occurring amino acid sequence.

The amino acid sequence for GLP-1 has been reported by several researchers. See Lopez, L. C. et al., 1983, *Proc. Natl. Acad. Sci.*, USA 80:5485-5489; Bell, G. I. et al., 1983, *Nature* 302:716-718; Heinrich, G. et al., 1984, *Endocrinol.* 115: 2176-2181. The structure of the preproglucagon mRNA and its corresponding amino acid sequence is well known. The proteolytic processing of the precursor gene product, proglucagon, into glucagon and the two insulinotropic peptides has been characterized. As used herein, the notation of GLP-1(1-37) refers to a GLP-1 polypeptide having all amino acids from 1 (N-terminus) through 37 (C-terminus). Similarly, GLP-1(7-37) refers to a GLP-1 polypeptide having all amino acids from 7 (N-terminus) through 37 (C-terminus). Similarly, GLP-1(7-36) refers to a GLP-1 polypeptide having all amino acids from number 7 (N-terminus) through number 36 (C-terminus).

In one embodiment, GLP-1(7-36) and its peptide fragments are synthesized by conventional means as detailed below, such as by the well-known solid-phase peptide synthesis described by Merrifield, J. M., 1962, *Chem. Soc.* 85:2149, and Stewart and Young, Solid Phase Peptide Synthesis, Freeman, San Francisco, 1969, pp. 27-66), which are incorporated by reference herein. However, it is also possible to obtain fragments of the proglucagon polypeptide, or of GLP-1, by fragmenting the naturally occurring amino acid sequence, using, for example, a proteolytic enzyme. Further, it is possible to obtain the desired fragments of the proglucagon peptide or of GLP-1 through the use of recombinant DNA technology, as disclosed by Maniatis, T., et al., Molecular Biology: A Laboratory Manual, Cold Spring Harbor, N.Y., 1982, which is hereby incorporated by reference.

Useful peptides for the methods described herein include those which are derivable from GLP-1 such as GLP-1(1-37) and GLP-1(7-36). A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Also useful are those molecules which are said to be "derivatives" of GLP-1 such as GLP-1(1-37) and especially GLP-1(7-36). Such a "derivative" has the following characteristics: (1) it shares substantial homology with GLP-1 or a similarly sized fragment of GLP-1; (2) it is capable of functioning as an insulinotropic hormone; and (3) using at least one of the assays provided herein, the derivative has an insulinotropic activity of at least 1%, 5%, 10%, 25% 50%, 75%, 100%, or greater than 100% of the insulinotropic activity of GLP-1.

A derivative of GLP-1 is said to share "substantial homology" with GLP-1 if the amino acid sequences of the derivative is at least 80%, and more preferably at least 90%, and most preferably at least 95%, the same as that of GLP-1(1-37).

Useful derivatives also include GLP-1 fragments which, in addition to containing a sequence that is substantially homologous to that of a naturally occurring GLP-1 peptide may contain one or more additional amino acids at their amino and/or their carboxy termini, or internally within said sequence. Thus, useful derivatives include polypeptide fragments of GLP-1 that may contain one or more amino acids that may not be present in a naturally occurring GLP-1 sequence provided that such polypeptides have an insulinotropic activity of at least 1%, 5%, 10%, 25% 50%, 75%, 100%, or greater than 100% of the insulinotropic activity of GLP-1. The additional amino acids may be D-amino acids or L-amino acids or combinations thereof.

Useful GLP-1 fragments also include those which, although containing a sequence that is substantially homologous to that of a naturally occurring GLP-1 peptide, lack one or more additional amino acids at their amino and/or their carboxy termini that are naturally found on a GLP-1 peptide. Thus, useful polypeptide fragments of GLP-1 may lack one or more amino acids that are normally present in a naturally occurring GLP-1 sequence provided that such polypeptides have an insulinotropic activity of at least 1%, 5%, 10%, 25% 50%, 75%, 100%, or greater than 100% of the insulinotropic activity of GLP-1. In certain embodiments, the polypeptide fragments lack one amino acid normally present in a naturally occurring GLP-1 sequence. In some embodiments, the polypeptide fragments lack two amino acids normally present in a naturally occurring GLP-1 sequence. In some embodiments, the polypeptide fragments lack three amino acids normally present in a naturally occurring GLP-1 sequence. In some embodiments, the polypeptide fragments lack four amino acids normally present in a naturally occurring GLP-1 sequence.

Also useful are obvious or trivial variants of the above-described fragments which have inconsequential amino acid substitutions (and thus have amino acid sequences which differ from that of the natural sequence) provided that such variants have an insulinotropic activity which is substantially identical to that of the above-described GLP-1 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

In addition to those GLP-1 derivatives with insulinotropic activity, GLP-1 derivatives which stimulate glucose uptake by cells but do not stimulate insulin expression or secretion are useful for the methods described herein. Such GLP-1 derivatives are described in U.S. Pat. No. 5,574,008, which is hereby incorporated by reference in its entirety.

GLP-1 derivatives which stimulate glucose uptake by cells but do not stimulate insulin expression or secretion which find use in the methods described herein include:

(SEQ ID NO: 3)
$H_2N$-Ser-Tyr-Leu-Glu-Gly-Gln-Ala-Ala-Lys-Glu-Phe-Ile-Ala-Trp-Leu-Val-Xaa-Gly-Arg-$R^2$;

(SEQ ID NO: 4)
$H_2N$-Ser-Ser-Tyr-Leu-Glu-Gly-Gln-Ala-Ala-Lys-Glu-Phe-Ile-Ala-Trp-Leu-Val-Xaa-Gly-Arg-$R^2$;

(SEQ ID NO: 5)
$H_2N$-Val-Ser-Ser-Tyr-Leu-Glu-Gly-Gln-Ala-Ala-Lys-Glu-Phe-Ile-Ala-Trp-Leu-Val-Xaa-Gly-Arg-$R^2$;

-continued

```
                                            (SEQ ID NO: 6)
H2N-Asp-Val-Ser-Ser-Tyr-Leu-Glu-Gly-Gln-Ala-Ala-
Lys-Glu-Phe-Ile-Ala-Trp-Leu-Val-Xaa-Gly-Arg-R2;

(SEQ ID NO: 7)
H2N-Ser-Asp-Val-Ser-Ser-Tyr-Leu-Glu-Gly-Gln-Ala-
Ala-Lys-Glu-Phe-Ile-Ala-Trp-Leu-Val-Xaa-Gly-
Arg-R2;

(SEQ ID NO: 8)
H2N-Thr-Ser-Asp-Val-Ser-Ser-Tyr-Leu-Glu-Gly-Gln-
Ala-Ala-Lys-Glu-Phe-Ile-Ala-Trp-Leu-Val-Xaa-
Gly-Arg-R2;

(SEQ ID NO: 9)
H2N-Phe-Thr-Ser-Asp-Val-Ser-Ser-Tyr-Leu-Glu-Gly-
Gln-Ala-Ala-Lys-Glu-Phe-Ile-Ala-Trp-Leu-Val-
Xaa-Gly-Arg-R2;

(SEQ ID NO: 10)
H2N-Thr-Phe-Thr-Ser-Asp-Val-Ser-Ser-Tyr-Leu-Glu-
Gly-Gln-Ala-Ala-Lys-Glu-Phe-Ile-Ala-Trp-Leu-
Val-Xaa-Gly-Arg-R2;

(SEQ ID NO: 11)
H2N-Gly-Thr-Phe-Thr-Ser-Asp-Val-Ser-Ser-Tyr-Leu-
Glu-Gly-Gln-Ala-Ala-Lys-Glu-Phe-Ile-Ala-Trp-
Leu-Val-Xaa-Gly-Arg-R2;

(SEQ ID NO: 12)
H2N-Glu-Gly-Thr-Phe-Thr-Ser-Asp-Val-Ser-Ser-Tyr-
Leu-Glu-Gly-Gln-Ala-Ala-Lys-Glu-Phe-Ile-Ala-
Trp-Leu-Val-Xaa-Gly-Arg-R2;

(SEQ ID NO: 13)
H2N-Ala-Glu-Gly-Thr-Phe-Thr-Ser-Asp-Val-Ser-Ser-
Tyr-Leu-Glu-Gly-Gln-Ala-Ala-Lys-Glu-Phe-Ile-
Ala-Trp-Leu-Val-Xaa-Gly-Arg-R2;

(SEQ ID NO: 14)
H2N-His-Ala-Glu-Gly-Thr-Phe-Thr-Ser-Asp-Val-Ser-
Ser-Tyr-Leu-Glu-Gly-Gln-Ala-Ala-Lys-Glu-Phe-
Ile-Ala-Trp-Leu-Val-Xaa-Gly-Arg-R2; and (SEQ ID NO: 15)
H2N-His-D-Ala-Glu-Gly-Thr-Phe-Thr-Ser-Asp-Val-
Ser-Ser-Tyr-Leu-Glu-Gly-Gln-Ala-Ala-Lys-
Glu-Phe-Ile-Ala-Trp-Leu-Val-Xaa-Gly-Arg-R2.
```

In the peptides, Xaa is selected from Lys and Arg and $R^2$ is selected from $NH_2$, OH, Gly-$NH_2$, and Gly-OH.

These peptides are C-terminal GLP-1 fragments which do not have insulinotropic activity but which are nonetheless useful for treating diabetes and hyperglycemic conditions as described in U.S. Pat. No. 5,574,008, which is hereby incorporated by reference in its entirety.

5.3.2 Exendin-3 and Exendin-4 Peptides

The exendin-3 and exendin-4 peptide can be any exendin-3 or exendin-4 peptide known to those of skill in the art. Exendin-3 and exendin-4 are 39 amino acid peptides (differing at residues 2 and 3) which are approximately 53% homologous to GLP-1 and find use as insulinotropic agents.

The native exendin-3 sequence is HSDGTFTSDL-SKQMEEEAVRLFIEWLKNGG PSSGAPPPS (SEQ ID NO:16) and the exendin-4 sequence is HGEGTFTSDL-SKQMEEEAVRLFIEWLKNGGPSSGAPPPS (SEQ ID NO:17).

Also useful for the methods described herein are insulinotropic fragments of exendin-4 comprising the amino acid sequences: exendin-4(1-31) desGlu$^{17}$ Tyr$^{32}$ (SEQ ID NO:18) HGEGTFTSDLSKQMEEAVRLFIEWLKNGGPY and exendin-4(1-30) Tyr$^{31}$ (SEQ ID NO:19) HGEGTFTSDL-SKQMEEEAVRLFIEWLKNGGY.

Also useful is the inhibitory fragment of native exendin-4 comprising the amino acid sequence: exendin-4(9-39) (SEQ ID NO:20) DLSKQMEEEAVRLFIEWLKNGGPSSGAP-PPS.

Other exemplary insulinotropic peptides are presented in SEQ ID NOS:21-27.

```
                                            SEQ ID NO:21
HDEFERHAEGTFTSDVSSYLEGQAAKEFIAWLVKGRK

SEQ ID NO:22
HAEGTFTSDVSSYLEGQAAKEFIAWLVKGRK

SEQ ID NO:23
HGEGTFTSDLSKQMEEEAVRLFIEWLKNGGPSSGAPPPSK

SEQ ID NO:24
HSDGTFTSDLSKQMEEEAVRLFIEWLKNGGPSSGAPPPSK

SEQ ID NO:25
HGEGTFTSDLSKEMEEEVRLFIEWLKNGGPY

SEQ ID NO:26
HGEGTFTSDLSKEMEEEVRLFIEWLKNGGY

SEQ ID NO:27
DLSKQMEEEAVRLFIEWLKGGPSSGPPPS
```

Useful peptides for the methods described herein include peptides which are derivable from the naturally occurring exendin-3 and exendin-4 peptides. A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Useful molecules for the methods described herein also include those which are said to be "derivatives" of exendin-3 and exendin-4. Such a "derivative" has the following characteristics: (1) it shares substantial homology with exendin-3 or exendin-4 or a similarly sized fragment of exendin-3 or exendin-4; (2) it is capable of functioning as an insulinotropic hormone and (3) using at least one of the assays provided herein, the derivative has an insulinotropic activity of at least 1%, 5%, 10%, 25% 50%, 75%, 100%, or greater than 100% of the insulinotropic activity of either exendin-3 or exendin-4.

A derivative of exendin-3 and exendin-4 is said to share "substantial homology" with exendin-3 and exendin-4 if the amino acid sequences of the derivative is at least 80%, and more preferably at least 90%, and most preferably at least 95%, the same as that of either exendin-3 or 4 or a fragment of exendin-3 or 4 having the same number of amino acid residues as the derivative.

Useful derivatives also include exendin-3 or exendin-4 fragments which, in addition to containing a sequence that is substantially homologous to that of a naturally occurring exendin-3 or exendin-4 peptide may contain one or more additional amino acids at their amino and/or their carboxy termini, or internally within said sequence. Thus, useful derivatives include polypeptide fragments of exendin-3 or exendin-4 that may contain one or more amino acids that may not be present in a naturally occurring exendin-3 or exendin-4 sequences provided that such polypeptides have an insulinotropic activity of at least 1%, 5%, 10%, 25% 50%, 75%, 100%, or greater than 100% of the insulinotropic activity of either exendin-3 or exendin-4.

Similarly, useful derivatives include exendin-3 or exendin-4 fragments which, although containing a sequence that is substantially homologous to that of a naturally occurring exendin-3 or exendin-4 peptide may lack one or more additional amino acids at their amino and/or their carboxy termini that are naturally found on a exendin-3 or exendin-4 peptide. Thus, useful derivatives include polypeptide fragments of exendin-3 or exendin-4 that may lack one or more amino acids that are normally present in a naturally occurring exendin-3 or exendin-4 sequence provided that such polypeptides have an insulinotropic activity of at least 1%, 5%, 10%, 25% 50%, 75%, 100%, or greater than 100% of the insulinotropic activity of either exendin-3 or exendin-4.

Useful derivatives also include the obvious or trivial variants of the above-described fragments which have inconsequential amino acid substitutions (and thus have amino acid sequences which differ from that of the natural sequence) provided that such variants have an insulinotropic activity which is substantially identical to that of the above-described exendin-3 or exendin-4 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

5.4 Conjugated insulinotropic peptides

Useful conjugated insulinotropic peptides for the methods described herein include insulinotropic peptides and their derivatives conjugated to a macromolecule. In preferred embodiments, the insulinotropic peptide is conjugated to albumin. Several methods can be used to link an insulinotropic peptide to albumin. In certain embodiments, the insulinotropic peptide is linked to albumin according to any technique known to those of skill in the art. In some embodiments, the insulinotropic peptide is modified to include a reactive group which can react with available reactive functionalities on albumin to form covalent linkages.

The reactive group is chosen for its ability to form a stable covalent bond with albumin, for example, by reacting with one or more amino groups, hydroxyl groups, or thiol groups on the serum protein or peptide. Preferably, a reactive group reacts with only one amino group, hydroxyl group, or thiol group on albumin. Preferably, a reactive group reacts with a specific amino group, hydroxyl group, or thiol group on albumin. A useful conjugate of the methods described herein comprises a modified peptide, or a modified derivative thereof, which is covalently attached to albumin via a reaction of the reactive group with an amino group, hydroxyl group, or thiol group on albumin. Thus, a useful conjugate comprises a modified peptide, or a modified derivative thereof, in which the reactive group has formed a covalent bond to albumin.

To form covalent bonds with the functional group on a protein, one may use as a chemically reactive group a wide variety of active carboxyl groups, particularly esters. The carboxyl groups are usually converted into reactive intermediates such as N-hydroxysuccinimide (NHS) or maleimide that are susceptible to attack by amines, thiols and hydroxyl functionalities on the protein. Introduction of NHS and maleimide reactive groups on the peptide can be performed by the use of bifunctionnal linking agents such as maleimide-benzoyl-succinimide (MBS) gamma-maleimido-butyryloxy succinimide ester (GMBS), dithiobis-N-hydrohy succinimido propropionate (DTSP), succinimidyl 3(2-pyridyldithio propionate) (SPDP), succinimidyl trans-4-(maleimidylmethyl) cyclohexane-1-carboxylate (SMCC), succinimidyl acetylthioacetate (SATA), benzophenone 4-maleimide, N-((2-pyridyldithio)ethyl)-4-azidosalicylamide (PEAS; AET). Such bifnctionnal linkers will activate either carboxy or amino group on the peptide based on the choice of protecting groups.

Alternatively the addition of maleimide to the peptide can be performed through the use of coupling agent such as N,N, dicyclohexylcarbodiimide (DCC), 1-ethyl-3-(3-dimethylaminopropyl) carbodiimide, hydrochloride (EDAC) and the likes to activate derivatives like maleimidopropionic acid, [2-[2-[2-maleimidopropionamido(ethoxy)ethoxy]acetic acid, and subsequently react with an amine on the peptide. Similar agents like DCC and EDAC could also be used to add derivatives like maleimidoalkyl amines to carboxy moieties on the peptide.

Primary amines are the principal targets for NHS esters. Accessible ε-amine groups present on the N-termini of proteins react with NHS esters. However, ε-amino groups on a protein may not be desirable or available for the NHS coupling. While five amino acids have nitrogen in their side chains, only the ε-amine of lysine reacts significantly with NHS esters. An amide bond can form when the NHS ester conjugation reaction reacts with primary amines releasing N-hydroxysuccinimide. These succinimidyl-containing reactive groups are herein referred to as succinimidyl groups.

In particular embodiments, the functional group on albumin is the single free thiol group located at amino acid residue 34 (Cys34) and the chemically reactive group is a maleimido-containing group such as MPA. MPA stands for maleimido propionic acid or maleimidopropionate. Such maleimido-containing groups are referred to herein as maleimido groups.

In some embodiments, albumin is covalently linked to a succinimidyl or maleimido group on the insulinotropic peptide. In some embodiments, an albumin amino, hydroxyl or thiol group is covalently linked to a succinimidyl or maleimido group on the insulinotropic peptide. In some embodiments, albumin cysteine 34 thiol is covalently linked via a [2-[2-[2-maleimidopropionamido(ethoxy)ethoxy]acetamide linker on the epsilon amino of a lysine of the insulinotropic peptide.

In a specific embodiment, the reactive group is a single MPA reactive group attached to the peptide, optionally through a linking group, at a single defined amino acid and the MPA is covalently attached to albumin at substantially a single amino acid residue of albumin, preferably cysteine 34. In a preferred embodiment, the albumin is recombinant human albumin. In certain embodiments, the reactive group, preferably MPA, is attached to the peptide through one or more linking groups, preferably AEEA, AEA, or octanoic acid. In certain examples of embodiments in which the reactive group, preferably MPA, is attached to the peptide through more than one linking group, each linking group can be independently selected from the group consisting preferably of AEA ((2-amino) ethoxy acetic acid), AEEA ([2-(2-amino) ethoxy)]ethoxy acetic acid), and octanoic acid. In one embodiment, the reactive group, preferably MPA, is attached to the peptide via 1, 2, 3, 4, 5 or 6 AEEA linking groups which are arranged in tandem. In another embodiment, the reactive group, preferably MPA, is attached to the peptide via 1, 2, 3, 4, 5 or 6 octanoic acid linking groups which are arranged in tandem. In certain embodiments, a linking group can comprise, for example, a chain of 0-30 atoms, or 0-20 atoms, or 0-10 atoms. In certain embodiments, a linking group can consist of, for example, a chain of 0-30 atoms, or 0-20 atoms, or 0-10 atoms. Those atoms can be selected from the group consisting of, for example, C, N, O, S, P.

In certain embodiments, the reactive group can be attached to any residue of the insulinotropic peptide suitable for attachment of such a reactive group. The residue can be a terminal or internal residue of the peptide. In certain embodiments, the reactive group can be attached to the carboxy-terminus or amino-terminus of the peptide. In advantageous embodiments, the reactive group is attached to a single site of the peptide. This can be achieved using protecting groups known to those of skill in the art. In certain embodiments, a derivative of the insulinotropic peptide can comprise a residue incorporated for attachment of the reactive group. Useful residues for attachment include, but are not limited to, lysine, aspartate and glutamate residues. The residue can be incorporated internally or at a terminus of the peptide. In certain embodiments, the reactive group is attached to an internal lysine residue. In certain embodiments, the reactive group is attached to a terminal lysine residue. In certain embodiments, the reactive group is attached to an amino-terminal lysine residue. In certain embodiments, the reactive group is attached to a carboxy-terminal lysine residue, for instance, a lysine residue at the carboxy-terminus of GLP-1, GLP-1(7-37) or exendin-4.

The manner of modifying insulinotropic peptides with a reactive group for conjugation to a macromolecule will vary widely, depending upon the nature of the various elements comprising the insulinotropic peptide. The synthetic procedures will be selected so as to be simple, provide for high yields, and allow for a highly purified product. Normally, the chemically reactive group will be created at the last stage of insulinotropic peptide synthesis, for example, with a carboxyl group, esterification to form an active ester. Specific methods for the production of modified insulinotropic peptides are described in U.S. Pat. Nos. 6,329,336, 6,849,714 or 6,887,849, the contents of which are hereby incorporated by reference in their entirety.

The conjugated insulinotropic peptides of the methods described herein may also be non-specifically conjugated to albumin. Bonds to amino groups will generally be employed, particularly with the formation of amide bonds for non-specific conjugation. To form such bonds, one may use as a chemically reactive group coupled to the insulinotropic peptide a wide variety of active carboxyl groups, particularly esters. While a number of different hydroxyl groups may be employed in these linking agents, the most convenient would be N-hydroxysuccinimide (NHS) and N-hydroxy-sulfosuccinimide (sulfo-NHS). Other linking agents which may be utilized are described in U.S. Pat. No. 5,612,034, which is hereby incorporated by reference in its entirety.

5.4.1 Insulinotropic Peptide Synthesis

Insulinotropic peptides may be synthesized by standard methods of solid phase peptide chemistry known to those of ordinary skill in the art. For example, insulinotropic peptides fragments may be synthesized by solid phase chemistry techniques following the procedures described by Steward and Young (Steward, J. M. and Young, J. D., 1984, Solid Phase Peptide Synthesis, 2nd Ed. (Pierce Chemical Company, Rockford, Ill.) using an Applied Biosystem synthesizer. Similarly, multiple fragments may be synthesized then linked together to form larger fragments. These synthetic peptide fragments can also be made with amino acid substitutions at specific locations. For solid phase peptide synthesis, a summary of the many techniques may be found in J. M. Stewart and J. D. Young, 1963, Solid Phase Peptide Synthesis. (W. H. Freeman Co., San Francisco), and J. Meienhofer, 1973, Hormonal Proteins and Peptides, vol. 2, p. 46, Academic Press, New York). For classical solution synthesis see G. Schroder and K. Lupke, The Peptides, Vol. 1, (Academic Press, New York). In some embodiments, synthesis of the insulinotropic peptides is as described in U.S. Pat. Nos. 6, 329,336, 6,849, 714 or 6,887,849, the contents of which are hereby incorporated by reference in their entirety.

5.4.2 Conjugation

Preferably, the peptide and macromolecule (preferably albumin) of the conjugates of the invention are present in the conjugate in a 1:1 molar ratio, or an approximately 1:1 molar ratio. In particular embodiments, the peptide and macromolecule (preferably albumin) of the conjugates of the invention are present in the conjugate in a 1:1 molar ratio. In a preferred embodiment, the peptide and serum protein are present in the conjugate in a 1:1 molar ratio, or an approximately 1:1 molar ratio, and the peptide is attached to the reactive group, optionally through a linking group, at substantially only one site on the peptide and the reactive group is attached to the serum protein at substantially only one site on the serum protein. In a particular embodiment, the peptide and serum protein are present in the conjugate in a 1:1 molar ratio and the peptide is attached to the reactive group, optionally through a linking group, at substantially only one site on the peptide and the reactive group is attached to the serum protein at substantially only one site on the serum protein.

Preferably, the serum protein is albumin. Preferably, the single site of attachment of the reactive group to albumin is preferably the thiol group of cysteine 34 of albumin (e.g., via a maleimide linkage). In a specific embodiment, the reactive group is a single MPA reactive group attached to the peptide, optionally through a linking group, at a single defined amino acid and the maleimide is covalently attached to albumin at substantially a single amino acid residue of albumin, preferably cysteine 34.

In a preferred embodiment, a conjugate of the invention is formed by contacting a modified peptide comprising a maleimido group with a thiol-containing serum protein, preferably albumin, under conditions comprising a pH of between about 4.0 to 8.0, preferably between about 5.0 to 8.0 and more preferably between about 6.0 to 7.2, thereby preferably forming a stable thioether linkage which cannot be cleaved under physiological conditions. In certain preferred embodiments, the serum protein is recombinant human albumin.

In one embodiment, the modified peptide is amidated at its C-terminal end. In another embodiment, the modified peptide is not amidated at its C-terminal end. A conjugate of the invention can also comprise such an amidated peptide.

In a preferred embodiment, a single reactive group is covalently attached at a defined site of the modified peptide. In a preferred embodiment of the conjugate, a single reactive group is covalently attached at a defined site of the modified peptide and the reactive group is covalently attached to a single defined site of albumin, preferably to the thiol group of amino acid residue Cys34 of albumin. Preferably, the reactive group of a modified peptide or conjugate of the invention comprises a maleimide group and forms peptide:albumin conjugates of approximately a 1:1 molar ratio. In certain embodiments, a 1:1 molar ratio of peptide to serum protein is preferred over higher ratios because a 1:1 molar ratio provides better biological activity than higher ratios (see e.g., Stehle et al. 1997 *Anti-Cancer Drugs* 8:677-685, incorporated herein in its entirety).

In a preferred embodiment, the albumin is recombinant human albumin. Specific methods for the production of preformed peptide: albumin conjugates are described in U.S. Provisional Application No. 60/791,241, the contents of which is hereby incorporated by reference in its entirety. Specific methods for the purification of peptide: albumin conjugates are described in U.S. Patent Application Publication No. 2005/0267293, the contents of which is hereby incorporated by reference in its entirety.

Albumin can be provided from different sources, such as purified from blood sample(s) and expressed by recombinant techniques including recombinant yeast or bacteria. In some embodiments, the albumin is serum albumin. In some embodiments, the albumin is human serum albumin. In some embodiments, the albumin is bovine serum albumin. In some embodiments, the albumin is recombinant serum albumin. In some embodiments, the albumin is recombinant human serum albumin. In some embodiments, the albumin is RECOMBUMIN® (Delta Biotechnology Ltd., Nottingham, U.K.). RECOMBUMIN® is a recombinant human albumin (rHA) that is produced in vitro using recombinant yeast technology, in which genetically modified yeast (Saccharomyces cerevisiae) secrete soluble rHA which is subsequently harvested, purified and formulated for use as an excipient for the manfacture of biologics or a coating for medical devices. The main advantage of rHA over HSA is that it is expressed in yeast with no human derived products used in the manufacturing process. The use of such controlled production methods leads to a purer product with less structural heterogeneity. Previous studies have indicated that there is no significant difference between soluble rHA and HSA in terms of their biochemical characteristics, radiolabelling efficiency and biological behavior in vitro and in vivo. See Dodsworth et al., 1996, *Biotechnol. Appl. Biochem.* 24: 171-176.

In certain embodiments, the conjugate is according to the following:

5.5 Monitoring the Presence of Conjugated Insulinotropic Peptides

The blood of the mammalian host may be monitored for the activity of the conjugated insulinotropic peptides and/or presence of the conjugated insulinotropic peptides using any method known to those of skill in the art. In certain embodiments, the conjugated insulinotropic peptides may be monitored using assays of insulinotropic activity. In other embodiments, the conjugated insulinotropic peptides may be monitored using HPLC-MS.

5.5.1 Assays of Insulinotropic Activity

The insulinotropic property of a conjugated insulinotropic peptide may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin.

Although any radioimmunoassay capable of detecting the presence of IRI may be employed, it is preferable to use a modification of the assay method of Albano et al., 1972, *Acta Endocrinol.* 70:487-509. In this modification, a phosphate/

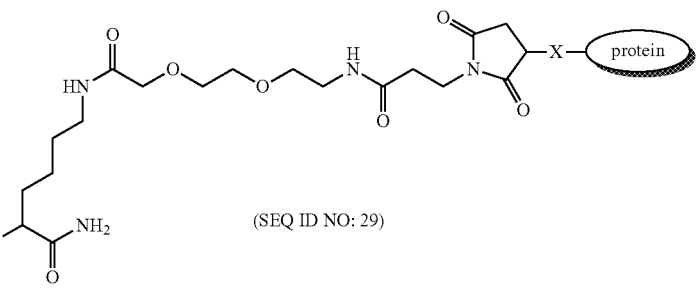

His-Gly-Glu-Gly-Thr-Phe-Thr-Ser-Asp-Leu-Ser-Lys-Gln-
Met-Glu-Glu-Glu-Ala-Val-Arg-Leu-Phe-Ile-Glu-Trp-Leu-
Lys-Asn-Gly-Gly-Pro-Ser-Ser-Gly-Ala-Pro-Pro-Pro-Ser (SEQ ID NO: 29)

wherein X is S, O, or NH of an amino acid of said protein. In certain embodiments, said protein is albumin. In certain embodiments, said protein is albumin and X is S of Cys 34 of said albumin. Albumin of the conjugate can be any albumin as described above.

In certain embodiments, the conjugate is according to the following:

albumin buffer with a pH of 7.4 is employed. The incubation is prepared with the consecutive condition of 500 μl of phosphate buffer, 50 μl of perfusate sample or rat insulin standard in perfusate, 100 μl of anti-insulin antiserum (Wellcome Laboratories; 1:40,000 dilution), and 100 μl of [$^{125}$I] insulin, giving a total volume of 750 μl in a 10×75-mm disposable

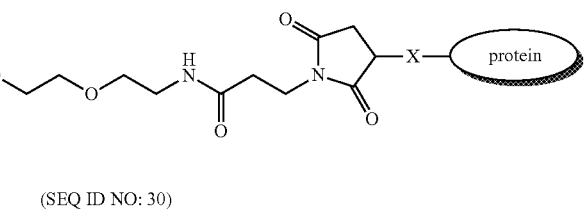

His-D-Ala-Glu-Gly-Thr-Phe-Thr-Ser-Asp-Val-
Ser-Ser-Tyr-Leu-Glu-Gly-Gln-Ala-Ala-Lys-
Glu-Phe-Ile-Ala-Trp-Leu-Val-Lys-Gly-Arg (SEQ ID NO: 30)

wherein X is S, O, or NH of an amino acid of said protein. In certain embodiments, said protein is albumin. In certain embodiments, said protein is albumin and X is S of Cys 34 of said albumin. Albumin of the conjugate can be any albumin as described above.

glass tube. After incubation for 2-3 days at 4° C., free insulin is separated from antibody-bound insulin by charcoal separation. The assay sensitivity is generally 1-2 μl U/ml. In order to measure the release of IRI into the cell culture medium of cells grown in tissue culture, one preferably incorporates radioactive label into proinsulin. Although any radioactive label capable of labeling a polypeptide can be used, it is preferable to use $^3$H leucine in order to obtain labeling of proinsulin. Labeling can be done for any period of time sufficient to permit the formation of a detectably labeled pool of proinsulin molecules; however, it is preferable to incubate cells in the presence of radioactive label for a 60-minute time period. Although any cell line capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a conjugated insulinotropic peptide may also be determined by pancreatic infusion. The in situ isolated perfused rat pancreas preparation is a modification of the method of Penhos et al., 1969, *Diabetes* 18:733-738. In accordance with such a method, fasted rats (preferably male Charles River strain albino rats), weighing 350-600 g, are anesthetized with an intraperitoneal injection of Amytal Sodium (Eli Lilly and Co., 160 ng/kg). Renal, adrenal, gastric, and lower colonic blood vessels are ligated. The entire intestine is resected except for about four cm of duodenum and the descending colon and rectum. Therefore, only a small part of the intestine is perfused, thus minimizing possible interference by enteric substances with insulinotropic immunoreactivity. The perfusate is preferably a modified Krebs-Ringer bicarbonate buffer with 4% dextran T70 and 0.2% bovine serum albumin (fraction V), and is preferably bubbled with 95% $O_2$ and 5% $CO_2$. A nonpulsatile flow, four-channel roller-bearing pump (Buchler polystatic, Buchler Instruments Division, Nuclear-Chicago Corp.) is preferably used, and a switch from one perfusate source to another is preferably accomplished by switching a three-way stopcock. The manner in which perfusion is performed, modified, and analyzed preferably follows the methods of Weir et al., 1974, *J. Clin. Investigat.* 54:1403-1412, which is hereby incorporated by reference.

5.5.2 HPLC-MS

HPLC coupled with mass spectrometry (MS) can be utilized to assay for the presence of conjugated insulinotropic peptides as is well known to the skilled artisan. Typically two mobile phases are utilized: 0.1% TFA/water and 0.1% TFA/acetonitrile. Column temperatures can be varied as well as gradient conditions. Particular details are disclosed in U.S. Pat. Nos. 6,887,849 and 6,329,336 which are hereby incorporated by reference.

6. EXAMPLES

The invention is illustrated by the following examples which are not intended to be limiting in any way.

6.1 Example 1

Conditioned Taste Aversion Test (CTA)

One model for studying gastrointestinal malaise in response to administration of a test agent is the conditioned taste aversion test (Peeters and Broekkamp, 1994, *J. Steroid Biochem. Mol. Biol.*, 49:417-427). Conditioned taste aversion is a form of associative learning in which animals learn to avoid flavors of substances where initial ingestion of the substance was followed by illness. In conditioned taste aversion, animals learn to associate a flavor, or conditioned stimulus, with the aversive effects of an administered agent, or unconditioned stimulus. Following conditioned stimulus—unconditioned stimulus pairings, animals reduce their consumption of the conditioned stimulus, and/or show a preference for other tastes when later presented with the conditioned flavor. A conditioned taste aversion test was performed to determine gastrointestinal malaise following administration of unconjugated exendin-4(1-39) versus exendin-4(1-39) Lys$^{40}$ ($\epsilon$-AEEA-MPA)-NH$_2$ conjugated with albumin (hereinafter called CJC-1134-PC in the following examples). The conditioned stimulus was 0.1% saccharin flavored water with high palatability. Lithium chloride was administered as a positive control for an unconditioned stimulus having an aversive gastrointestinal effect. See Riley and Baril, 1976, *Anim. Learn. Behav.* 4:1S-13S; Olivier et al., 1999, *Pharmacol. Biochem. Behav.* 64:213-220.

Eighty male Sprague-Dawley rats of 6 weeks in age were divided into eight dosing groups (n=10/group). On the day of dosing, food and water were removed at 0900 h. At 1300 h, all rats were offered 0.1% saccharin (the conditioned stimulus) for four hours. At 1700 h, the saccharin solution was removed and test agents (unconditioned stimuli) were administered accordingly: group 1: vehicle, 0.9% NaCl, subcutaneous injection (SC); group 2: LiCl, 80 mg/kg, intraperitoneal injection (IP); group 3: CJC-1134-PC, 0.0125 nmol/kg (0.9 µg/kg), SC; group 4: CJC-1134-PC, 0.5 nmol/kg (35 µg/kg), SC; group 5: CJC-1134-PC, 2 nmol/kg (140 µg/kg), SC; group 6: human serum albumin, 0.5 nmol/kg (32.5 µg/kg), SC; group 7: exendin-4, 0.5 nmol/kg (2 µg/kg), SC; and group 8: exendin-4, 0.5 mnol/kg (2 µg/kg), IP.

Following injection, all groups were given food ad libitum and 2 bottles of water. At 72 h and 96 h post dose, a choice of tap water or 0.1% saccharin solution (conditioned stimulus) was offered, and intake of both solutions was measured for 12 hours. Mean saccharin preference ratios, representing the percentage of saccharin solution consumed relative to total liquid intake, were determined for each group (FIGS. 1 and 2).

CJC-1134-PC induced a significantly lower taste aversion response compared to unconjugated exendin-4. While saccharin solution consumption in rats dosed with unconjugated exendin-4 (0.5 nmol/kg, SC) represented only ~40% of the total liquid intake for the 12 h period beginning 72 h post dose, saccharin solution consumption in rats receiving CJC-1134-PC (0.5 nmol/kg, SC) represented over 80% of the total liquid intake over the same period. Similar results were observed at 96 h post dose (FIG. 2). These results indicate a significant reduction in gastrointestinal malaise in response to CJC-1134-PC compared to unconjugated exendin-4. None of the three CJC-1134-PC doses resulted in conditioned taste aversion because there no statistically significant difference in saccharin preference ratios when compared to the internal negative vehicle control. On the contrary, exendin-4 decreased significantly the preference saccharine ratio as compared to the vehicle group aversion.

6.2 Example 2

Kaolin Intake

Another model for assessing gastrointestinal malaise in the rat is the consumption of non-nutritive substances following administration of a toxic agent. Pica, the ingestion of dirt or a non-nutritive clay such as kaolin, is a behavior only observed when rats are thought to be ill. As rats appear to lack an emetic reflex, kaolin ingestion has been used as an indirect indicator of nausea in response to a toxic agent. Accordingly, kaolin ingestion was measured in rats injected with unconjugated exendin-4 versus CJC-1134-PC to assess tolerability.

Ninety male Sprague-Dawley rats of 6 weeks in age were housed individually and given food and water ad libitum. Habituation to kaolin was achieved by offering fresh blocks of kaolin daily for 8 days before dosing. Rats were then assigned to nine treatment groups (n=10/group). On the day of dosing (0900 h), rats were given clean cages with minimal bedding, and test agents were administered accordingly: group 1: vehicle, 0.9% NaCl, SC; group 2: LiCl, 80 mg/kg, IP; group 3: CJC-1134-PC, 0.125 nmol/kg (9 µg/kg), SC; group 4: CJC-1134-PC, 0.5 nmol/kg (35 µg/kg), SC; group 5: CJC-1134-PC, 2 nmol/kg (140 µg/kg), SC; group 6: human serum albumin, 0.5 nmol/kg (32.5 µg/kg), SC; group 7: exendin-4, 0.5 nmol/kg (2 µg/kg), SC; group 8: exendin-4, 0.5 nmol/kg (2 µg/kg), IP; and group 9: LiCl, 127 mg/kg, IP.

Immediately following injection, animals were offered a fresh kaolin block in addition to food and water. Kaolin intake was measured every hour for a four-hour period immediately after dosing, and also at 6, 8, and 24 hours post dose (FIG. 3).

Gastrointestinal malaise was immediate in rats receiving LiCl as indicated by significant kaolin intake after 1 h. Minimal kaolin intake was observed for the first 2 h in rats receiving both exendin-4 and CJC-1134-PC relative to 0.9% NaCl; however, intake dramatically increased by 3 h post dose in exendin-4 treated rats (0.5 nmol/kg SC). In CJC-1134-PC treated rats (0.5 nmol/kg SC), kaolin intake was only moderately increased after 6 h relative to 0.9% NaCl treated rats, thus indicating an increased tolerability of CJC-1134-PC compared to unconjugated exendin-4.

6.3 Example 3

Toxicity Studies

Toxicity of CJC-1134-PC was assessed in 7-day and 28-day studies utilizing both rat and primate subjects. CJC-1134-PC was administered daily by subcutaneous injection.

6.3.1 Rat Toxicity Study

For the 7-day study, Sprague Dawley rats were divided into four dosing groups (n=5/sex/group), and CJC-1134-PC was injected at 0, 1, 5 or 25 mg/kg/day SC. Immediately following injection, rats were housed individually, and food consumption and changes in body weights were monitored. Overall, no mortality or serious signs of toxicity were observed throughout the 7-day period. A dose dependent decrease in food consumption was observed at days 1-3 in rats dosed at 5 and 25 mg/kg/day. However, by day 4, food consumption was similar to that observed in rats receiving vehicle only (FIG. 4). Similar decreases in water consumption and body weight were observed in rats dosed at 5 and 25 mg/kg/day; however recovery was observed by days 3-4. (FIG. 5). There were no effects on clinical chemistry, hematology, urinalysis, or organ weights, or on macroscopic evaluations.

For the 28-day study, rats were divided into five dosing groups (n=10 or 15/sex/group), and CJC-1134-PC was injected at 0, 1, 5 or 25 mg/kg/day SC. Recombinant human albumin (rHA) was also dosed at 23 mg/kg as an additional control.

Following injections, a transient decrease in activity and fecal output was observed. A decrease in food consumption was observed at 25 mg/kg from days 1-7 (FIG. 6). However, by day 8, food consumption was comparable across all dosing groups. Decreases in body weight were also observed at the 25 mg/kg/doses at days 1-4. However, weight gain was comparable across all dosing groups from days 4-28 (FIG. 7). There were no effects on macroscopic evaluations. CJC-1134-PC was generally well tolerated in rats at up to 25 mg/kg.

6.3.2 Monkey Toxicity Study

For the 7-day study, monkeys were divided into 4 dosing groups (n=2/sex/group), and CJC-1134-PC was injected at 0, 0.4, 2, and 10 mg/kg/day SC. Overall, no mortality or serious signs of toxicity were observed throughout the 7-day period. Initial decreases in food consumption, as measured by the number of biscuits consumed per day, were observed across all dosing groups including vehicle control for days 1-3. By days 4-7, food consumption was comparable across all dosing groups (FIG. 8). There was a dose-dependent decrease in body weight by day 3 which was moderately attenuated by day 7 (FIG. 9). There were no effects on clinical chemistry, hematology, urinalysis, or organ weights, or on macroscopic evaluations.

For the 28-day study, monkeys were divided into 5 dosing groups (n=3 or 6/sex/group), and CJC-1134-PC was injected at 0, 0.4, 2, 10 mg/kg/day SC. Recombinant human albumin was also dosed at 9 mg/kg as an additional control. Food consumption was significantly reduced at 10/mg/kg on days 2 and 3 (FIG. 10). A transient decrease in activity, hunched posture, and decreased fecal output were also observed. However, food consumption was comparable across all dosing groups by day 7. A dose dependent decrease in body weight was observed throughout the 28-day period (FIG. 11). There were no effects on macroscopic evaluations. CJC-1134-PC was generally well tolerated in monkeys up to 10 mg/kg.

6.4 Example 4

Diabetes Test

The efficacy of CJC-1134-PC to treat diabetes was examined in 7 week-old female diabetic db/db mice (body weight range: 30.3 to 34.0 g; glycemia range: 8.6 to 21.9 mmol/L, pre-dose). Mice were divided into four groups and injected once by subcutaneous bolus injection (dose volume of 8 ml/kg) accordingly: group 1: vehicle, 0.9% NaCl, n=3; group 2: CJC-1134-PC, 100 nmol/kg (7105 µg/kg), n=5; group 3: exendin-4, 100 nmol/kg (418 µg/kg), n=5; and group 4: exendin-4, 1 nmol/kg (4 µg/kg), n=5.

Blood glycemia was recorded at the following time points: pre-dose, 1, 3, 6, 24, 30, 48, 52, 74 and 101 hours post dose using a handheld glucometer (Accu-check compact, Roche Diagnostics, Canada). Food and water intake were recorded at the following timepoints: 0 to 6, 6 to 24, 24 to 30, 30 to 48, 48 to 72 and 72 to 101 hours post dose.

At 24 h post dose, blood glucose levels were significantly lower in mice receiving 100 nmol/kg CJC-1134-PC compared to 100 nmol/kg unconjugated exendin-4 (FIG. 12), and remained lower out to 48 h post dose (FIG. 13). After 72 h, blood glucose levels in CJC-1134-PC-treated mice were comparable to those observed in unconjugated exendin-4-treated mice (FIG. 14).

Food and water consumption was significantly reduced in mice dosed with CJC-1134-PC compared to unconjugated exendin-4 after 24 hours, and remained lower during the period of 24-47 h post dose (FIG. 15 and FIG. 16). After 74 h, food consumption was only moderately lower in CJC-1134-PC treated mice relative to exendin-4 treated mice, and this difference was maintained out to 101 h post dose (FIG. 15). Water consumption remained moderately lower for CJC- 1134-PC treated mice out to 101 h post dose (FIG. 16). No abnormal clinical signs were recorded during the study.

6.5 Example 5

Anti-Obesity Tests

The effect of CJC-1134-PC and unconjugated exendin-4 on body weight gain and food intake was assessed in a diabetic obese rat model. Male Zucker Diabetic Fatty (ZDF) rats were divided into five groups and received four weekly subcutaneous injections accordingly: group 1: vehicle, 0.9% NaCl, n=8; group 2: exendin-4, 100 nmol/kg (418 µg/kg), n=8; group 3: exendin-4, 200 nmol/kg (836 µg/kg), n=8; group 4: CJC-1134-PC, 100 nmol/kg (7.1 mg/kg), n=8; and group 5: CJC-1134-PC, 200 nmol/kg (14.2 mg/kg), n=8.

Control animal were injected with 0.9% NaCl. Animals were weighed twice a week and food intake was measured daily for the first week and four times a week thereafter for a total of 25 days. Statistical analysis was performed using two-way Analysis of Variance (ANOVA) followed by the Tukey's pair-wise comparison test. Significance was considered when P value was less than 0.05.

Cumulative weight gain was significantly reduced in rats dosed with CJC-1134-PC compared to 0.9% NaCl (FIG. 17). Statistical significance was observed at 200 nmol/kg CJC-1134-PC beginning at day 4 ($p \leq 0.01$), and at 100 nmol/kg CJC-1134-PC beginning at day 11 ($p \leq 0.05$); significance at both doses was maintained for the duration of the study. While cumulative weight gain was also reduced in unconjugated exendin-4 treated rats compared to 0.9% NaCl, this decrease was not significant compared to the 0.9% NaCl group.

Reduction in cumulative food intake was observed in both CJC-1134-PC treated as well as unconjugated exendin-4 treated rats relative to the 0.9% NaCl group. However, this decrease reached statistical significance in CJC-1134-PC treated rats after the second injection, on day 9, while statistical significance was not observed until after the third injection, on day 16, in exendin-4 treated rats (FIG. 18).

6.6 Example 6

Incidence of Nausea and Vomiting in Type 2 Diabetic Patients: Exenatide Versus CJC-1134-PC

6.6.1 Exenatide

Calara et al., 2005, *Clin. Ther*. 27(2): 210-214, conducted a randomized open-label crossover study examining the effect of injection site on bioavailability of exenatide (synthetic exendin-4). It was reported by the authors that three patients who received an inadvertent 10-fold overdose of exenatide (100 µg i.e., 24 nmoles) experienced severe nausea and vomiting, with one patient experiencing severe hypoglycemia requiring aid. In patients receiving a normal 10 µg (2.4 nmoles) dose of exenatide, mild to moderate nausea was experienced by 36%, and vomiting by 21% of patients respectively.

Additionally, in three different Phase III clinical trials of exenatide, which enrolled a total of 1446 patients (480 patients receiving Exenatide 5 µg BID, 483 receiving Exenatide 10 µg BID, and 483 patients receiving placebo for 30 weeks), the most commonly reported treatment-emergent adverse events were nausea, at an incidence of 43.5%. See Iltz et al., 2006, *Clin. Ther*. 28(5): 652-665. The incidence of severe nausea associated with Exenatide therapy ranged from 2% to 5% in each of the 3 trials. Severe nausea generally occurred more frequently in the groups that received Exenatide 10 µg compared to those that received Exenatide 5 µg. Withdrawals attributed to nausea occurred in 2% to 4% of patients in the Exenatide arms across the 3 trials, again generally more frequently in the groups that received 10 µg compared to those that received 5 µg. Otherwise, reported nausea was generally mild to moderate and occurred with greater frequency during the first 8 weeks of therapy compared to the last 22 weeks.

Currently, exenatide is prescribed at 5 or 10 µg per dose twice a day.

6.6.2 CJC-1134-PC

A Phase I/II single escalating dose clinical study for the treatment of Type 2 diabetes using CJC-1134-PC was conducted to evaluate safety and tolerability, and as a secondary endpoint, the pharmacokinetic and pharmacodynamic (duration of activity after one injection based on mean glucose reductions) profile of CJC-1134-PC in patients with stable Type 2 diabetes.

Patients enrolled in the trial had HbA1c levels between 6.5% and 11%. Patients previously treated with oral antidiabetic agents discontinued therapy at least 1 week prior to dosing. Six cohorts were dosed subcutaneously at 310, 620, 1250, 2500, 5000 and 3750 µg of CJC-1134-PC. Injections were performed with a 29 gauge needle. Each cohort consisted of 7 patients (6 active, 1 placebo). The mean glucose values at baseline of the cohorts (without placebo) were 15.6, 12.2, 12.1, 11.2, 9.6 and 15.3 mmol/L, respectively.

6.6.2.1 Safety and Tolerability

There were no safety or tolerability issues reported in the first four cohorts (310, 620, 1250 and 2500 µg dose), specifically, no nausea, no vomiting and no injection site reactions. At the 5000 microgram cohort, symptoms linked to an over stimulation of the GLP-1 receptors were observed as a result of the rapid decrease in blood glucose (manifested by headache, dizziness, and light-headedness without documented hypoglycaemia). In view of the positive activity demonstrated at the 1250 and 2500 microgram cohorts, 3750 micrograms of drug was dosed. In each of the 3750 and 5000 µg cohorts, there was one mild and transient case of short-term gastric stasis (observed post-lunch on day one); no anti-emetic medications were needed for either of these cases nor were any anti-emetics needed throughout the trial.

6.6.2.2 Pharmacokinetic Profile

The pharmacokinetic profile exhibited slow absorption and a prolonged exposure, with plasma drug levels rising for 4 to 6 days and then declining thereafter. For the 310 and 620 µg cohorts, the plasma concentration declined slowly for approximately 1 to 2 weeks following the plasma peak. Plasma concentrations were dose linear. Mean terminal half-life ranged from 164 hours to 274 hours and was not dose-dependent.

6.6.2.3 Efficacy

The efficacy parameters were based on the group mean and individual mean glucose values. Glucose was measured 6 times per day (fasting, 2-hour post-breakfast, pre-lunch, 2-hour post-lunch, pre-dinner and bedtime) during the first week and 3 times per day (fasting, 2-hour post-breakfast and bedtime) for the remaining 5 weeks of the study. In addition, a placebo group was constructed for data analysis by pooling the patients (one per cohort) that received placebo during the study. Limited or no efficacy was observed in the first two cohorts (310 and 620 micrograms). At the third cohort (1250 micrograms), the mean glucose reduction from baseline for the first week was 19% (ranging from 15% to 24% with a mean reduction on day 7 of 20%), giving an average glucose value for the week of 9.8 mmol/L. This glucose reduction was significant against baseline (p=0.0007) and against placebo (p=0.0045). Prolonged glucose lowering effect was observed for more than 2 weeks. The glucose reductions of the subsequent cohorts were of similar magnitude and duration and confirmed this response. At the 2500 microgram cohort, the average glucose value for the first week was reduced to 9.5 mmol/L; the value for the 5000 microgram cohort for the first week was reduced to 8.4 mmol/L. (The American Diabetes Association (ADA) has a recommended target of HbA1C<7%; a mean daily glucose level of 9.5 mmol/L corresponds to an HbA1C level of 7%). Furthermore, weight reduction was observed during the first week: average loss of 0.3 kg at day 7 for the placebo group, average loss of 0.4 kg at day 7 for the first two non-active cohorts had an average loss of 0.9 kg at day 7 for the three following cohorts where activity was observed on glucose.

A comparison of the incidence of nausea and vomiting in Type 2 diabetic patients injected with a single subcutaneous injection of Exenatide versus CJC-1134-PC is represented in TABLE 1.

TABLE 1

| Drug | N | Dose (μg) | Dose (nmoles) | Nausea (%) | Vomiting (%) |
|---|---|---|---|---|---|
| Exenatide | 25 | 10 | 2.4 | 36% | 21% |
|  | 3 | 100 | 24 | 100% | 100% |

TABLE 1-continued

| Drug | N | Dose (μg) | Dose (nmoles) | Nausea (%) | Vomiting (%) |
|---|---|---|---|---|---|
| CJC-1134-PC | 6 | 310 | 4.4 | 0 | 0 |
|  | 6 | 620 | 8.7 | 0 | 0 |
|  | 6 | 1250 | 17.6 | 0 | 0 |
|  | 6 | 2500 | 35.2 | 0 | 0 |
|  | 6 | 3750 | 52.8 | 17% | 17% |
|  | 6 | 5000 | 70.4 | 50% | 17% |

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of administering an exendin-4 peptide to a nausea-sensitive subject comprising subcutaneously administering to said nausea-sensitive subject the exendin-4 peptide conjugated to albumin, wherein the administration of the conjugated exendin-4 peptide to an animal reduces nausea compared to administration of the unconjugated exendin-4 peptide to the animal, and wherein the conjugated exendin-4 peptide is a conjugate (SEQ ID NO:28) according to the following formula:

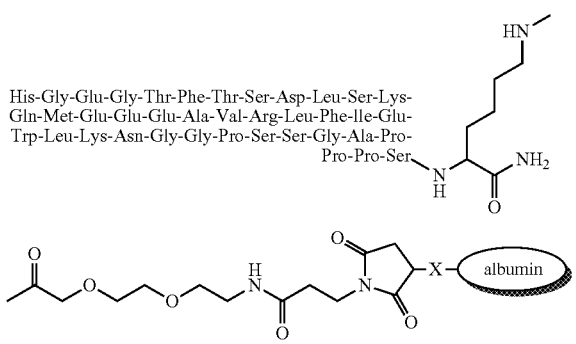

wherein X is S of Cysteine 34 of human serum albumin.

2. The method of claim 1 further comprising the step of selecting the nausea-sensitive subject prior to administering said exendin-4 peptide conjugated to albumin.

3. The method of claim 1 wherein said nausea-sensitive subject is nausea sensitive as a result of having been administered an unconjugated exendin-4 peptide, wherein said exendin-4 peptide is SEQ ID NO:12.

4. The method of claim 1 wherein said administering of the conjugated exendin-4 peptide prevents nausea in the subject.

5. The method of claim 1 which comprises administering the conjugated exendin-4 peptide in an amount between 1000 and 4000 μg, and wherein the nausea-sensitive subject is a human.

6. The method of claim 1 which comprises administering the conjugated exendin-4 peptide in an amount between 1250 and 3750 μg, and wherein the nausea-sensitive subject is a human.

7. The method of claim 1 which comprises administering the conjugated exendin-4 peptide in an amount between 1250 and 2500 μg, and wherein the nausea-sensitive subject is a human.

8. The method of claim 1 which comprises administering the conjugated exendin-4 peptide in an amount of 1250 μg, and wherein the nausea-sensitive subject is a human.

9. The method of claim 1 which comprises administering the conjugated exendin-4 peptide in an amount of 2500 μg, and wherein the nausea-sensitive subject is a human.

10. The method of claim 1 which comprises administering the conjugated exendin-4 peptide in an amount of 3750 μg, and wherein the nausea-sensitive subject is a human.

11. The method of claim 1 wherein said administering of the conjugated exendin-4 peptide is in an amount effective to treat a disease or disorder that is characterized by the fact that it is treatable by the action of said unconjugated exendin-4 peptide.

12. The method of claim 11 wherein the disease or disorder is obesity or diabetes.

13. The method of claim 12 wherein the disease or disorder is obesity.

14. The method of claim 12 wherein the disease or disorder is diabetes.

15. The method of claim 14 wherein the disease or disorder is type II diabetes.

16. The method of claim 1 wherein the subject is human.

17. The method of claim 1 wherein the human serum albumin is recombinant human serum albumin.

18. The method of claim 1 wherein the conjugated exendin-4 peptide is purified.

19. The method of claim 1 which comprises administering the conjugated exendin-4 peptide in an amount of 1500 μg, and wherein the nausea-sensitive subject is a human.

20. The method of claim 1 which comprises administering the conjugated exendin-4 peptide in an amount of 2000 μg, and wherein the nausea-sensitive subject is a human.

21. The method of claim 1 which comprises administering the conjugated exendin-4 peptide in an amount of 3000 μg, and wherein the nausea-sensitive subject is a human.

22. The method of claim 1, wherein the subject is experiencing nausea at the time of said administering.

23. A method of administering an exendin-4 peptide to a subject comprising (a) selecting a nausea sensitive subject having a disease or disorder treatable with the exendin-4 peptide; and (b) subcutaneously administering to the subject the exendin-4 peptide conjugated to albumin wherein administration of the conjugated exendin-4 peptide to an animal reduces nausea compared to administration of the unconjugated exendin-4 peptide to the animal, and wherein the conjugated exendin-4 peptide is a conjugate (SEQ ID NO:28) according to the following formula:

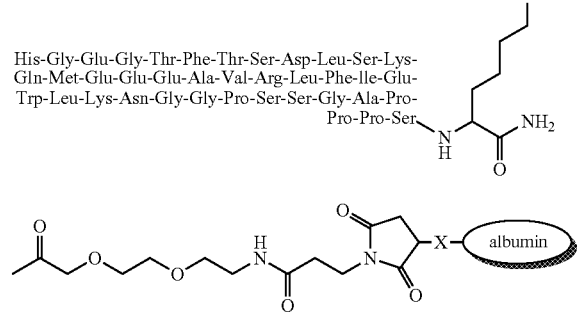

wherein X is S of Cysteine 34 of human serum albumin.

24. A method for the treatment of diabetes or obesity in a subject, comprising:

(a) selecting a nausea-sensitive subject in need of said treatment, and (b) subcutaneously administering an exendin-4 peptide conjugated to albumin to the selected subject, wherein the administration of the conjugated exendin-4 peptide to an animal provides a reduced nausea side effect compared to the administration of the exendin-4 peptide alone to the animal, and wherein the conjugated exendin-4 peptide is a conjugate (SEQ ID NO:28) according to the following formula:

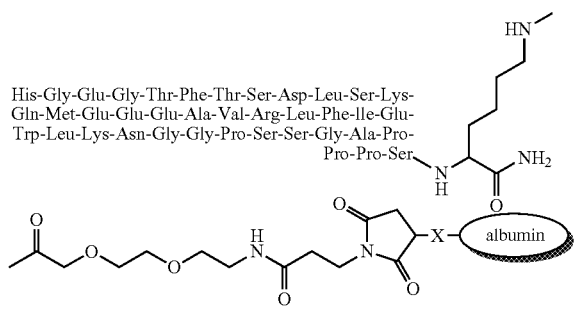
wherein X is S of Cysteine 34 of human serum albumin.
25. The method of claim 24, wherein the disease is diabetes.
26. The method of claim 24, wherein the disease is obesity.
27. The method of claim 24, wherein the human serum albumin is recombinant human serum albumin.
28. The method of any one of claims 1, 23 and 24, wherein the subject is a human, and wherein the conjugated exendin-4 peptide is purified.
* * * * *

SEQUENCE LISTING

```
<160> NUMBER OF SEQ ID NOS: 30

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 31
<212> TYPE: PRT
<213> ORGANISM: Artificial sequence
<220> FEATURE:
<223> OTHER INFORMATION: Description of Artificial Sequence: synthetic
      peptide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 20
```

```
<212> TYPE: PRT
<213> ORGANISM: Artificial Sequence
<220> FEATURE:
<221> NAME/KEY: VARIANT
<222> LOCATION: 17
<223> OTHER INFORMATION: Xaa = Lys or Arg
<220> FEATURE:
<221> NAME/KEY: VARIANT
<222> LOCATION: 20
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 3

Ser Tyr Leu Glu Gly Gln Ala Ala Lys Glu Phe Ile Ala Trp Leu Val
 1               5                  10                  15

Xaa Gly Arg Xaa
            20

<210> SEQ ID NO 4
<211> LENGTH: 21
<212> TYPE: PRT
<213> ORGANISM: Artificial sequence
<220> FEATURE:
<221> NAME/KEY: VARIANT
<222> LOCATION: 18
<223> OTHER INFORMATION: Xaa = Lys or Arg
<220> FEATURE:
<221> NAME/KEY: VARIANT
<222> LOCATION: 21
<223> OTHER INFORMATION: Xaa = X1-R1 where X1 is Gly or Absent and R1 is
      NH2 or OH
<220> FEATURE:
<223> OTHER INFORMATION: Description of Artificial sequence: synthetic
      peptide

<400> SEQUENCE: 4

Ser Ser Tyr Leu Glu Gly Gln Ala Ala Lys Glu Phe Ile Ala Trp Leu
 1               5                  10                  15

Val Xaa Gly Arg Xaa
            20

<210> SEQ ID NO 5
<211> LENGTH: 22
<212> TYPE: PRT
<213> ORGANISM: Artificial Sequence
<220> FEATURE:
<221> NAME/KEY: VARIANT
<222> LOCATION: 19
<223> OTHER INFORMATION: Xaa = Lys or Arg
<220> FEATURE:
<221> NAME/KEY: VARIANT
<222> LOCATION: 22
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 5

Val Ser Ser Tyr Leu Glu Gly Gln Ala Ala Lys Glu Phe Ile Ala Trp
 1               5                  10                  15

Leu Val Xaa Gly Arg Xaa
            20

<210> SEQ ID NO 6
<211> LENGTH: 23
<212> TYPE: PRT
<213> ORGANISM: Artificial sequence
```

```
<220> FEATURE:
<221> NAME/KEY: VARIANT
<222> LOCATION: 20
<223> OTHER INFORMATION: Xaa = Lys or Arg
<220> FEATURE:
<221> NAME/KEY: VARIANT
<222> LOCATION: 23
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 6

Asp Val Ser Ser Tyr Leu Glu Gly Gln Ala Ala Lys Glu Phe Ile Ala
 1               5                  10                  15

Trp Leu Val Xaa Gly Arg Xaa
             20

<210> SEQ ID NO 7
<211> LENGTH: 24
<212> TYPE: PRT
<213> ORGANISM: Artificial sequence
<220> FEATURE:
<221> NAME/KEY: VARIANT
<222> LOCATION: 21
<223> OTHER INFORMATION: Xaa = Lys or Arg
<220> FEATURE:
<221> NAME/KEY: VARIANT
<222> LOCATION: 24
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 7

Ser Asp Val Ser Ser Tyr Leu Glu Gly Gln Ala Ala Lys Glu Phe Ile
 1               5                  10                  15

Ala Trp Leu Val Xaa Gly Arg Xaa
             20

<210> SEQ ID NO 8
<211> LENGTH: 25
<212> TYPE: PRT
<213> ORGANISM: Artificial Sequence
<220> FEATURE:
<221> NAME/KEY: VARIANT
<222> LOCATION: 22
<223> OTHER INFORMATION: Xaa = Lys or Arg
<220> FEATURE:
<221> NAME/KEY: VARIANT
<222> LOCATION: 25
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 8

Thr Ser Asp Val Ser Ser Tyr Leu Glu Gly Gln Ala Ala Lys Glu Phe
 1               5                  10                  15

Ile Ala Trp Leu Val Xaa Gly Arg Xaa
             20                  25

<210> SEQ ID NO 9
<211> LENGTH: 26
<212> TYPE: PRT
<213> ORGANISM: Artificial sequence
<220> FEATURE:
<221> NAME/KEY: VARIANT
```

```
<222> LOCATION: 23
<223> OTHER INFORMATION: Xaa = Lys or Arg
<220> FEATURE:
<221> NAME/KEY: VARIANT
<222> LOCATION: 26
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 9

Phe Thr Ser Asp Val Ser Ser Tyr Leu Glu Gly Gln Ala Ala Lys Glu
 1               5                  10                  15

Phe Ile Ala Trp Leu Val Xaa Gly Arg Xaa
             20                  25

<210> SEQ ID NO 10
<211> LENGTH: 27
<212> TYPE: PRT
<213> ORGANISM: Artificial Sequence
<220> FEATURE:
<221> NAME/KEY: VARIANT
<222> LOCATION: 24
<223> OTHER INFORMATION: Xaa = Lys or Arg
<220> FEATURE:
<221> NAME/KEY: VARIANT
<222> LOCATION: 27
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 10

Thr Phe Thr Ser Asp Val Ser Ser Tyr Leu Glu Gly Gln Ala Ala Lys
 1               5                  10                  15

Glu Phe Ile Ala Trp Leu Val Xaa Gly Arg Xaa
             20                  25

<210> SEQ ID NO 11
<211> LENGTH: 28
<212> TYPE: PRT
<213> ORGANISM: Artificial sequence
<220> FEATURE:
<221> NAME/KEY: VARIANT
<222> LOCATION: 25
<223> OTHER INFORMATION: Xaa = Lys or Arg
<220> FEATURE:
<221> NAME/KEY: VARIANT
<222> LOCATION: 28
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 11

Gly Thr Phe Thr Ser Asp Val Ser Ser Tyr Leu Glu Gly Gln Ala Ala
 1               5                  10                  15

Lys Glu Phe Ile Ala Trp Leu Val Xaa Gly Arg Xaa
             20                  25

<210> SEQ ID NO 12
<211> LENGTH: 29
<212> TYPE: PRT
<213> ORGANISM: Artificial Sequence
<220> FEATURE:
<221> NAME/KEY: VARIANT
<222> LOCATION: 26
<223> OTHER INFORMATION: Xaa = Lys or Arg
```

```
<220> FEATURE:
<221> NAME/KEY: VARIANT
<222> LOCATION: 29
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 12

Glu Gly Thr Phe Thr Ser Asp Val Ser Ser Tyr Leu Glu Gly Gln Ala
 1               5                  10                  15

Ala Lys Glu Phe Ile Ala Trp Leu Val Xaa Gly Arg Xaa
            20                  25

<210> SEQ ID NO 13
<211> LENGTH: 30
<212> TYPE: PRT
<213> ORGANISM: Artificial Sequence
<220> FEATURE:
<221> NAME/KEY: VARIANT
<222> LOCATION: 27
<223> OTHER INFORMATION: Xaa = Lys or Arg
<220> FEATURE:
<221> NAME/KEY: VARIANT
<222> LOCATION: 30
<223> OTHER INFORMATION: Xaa = X1-R1 where X1 is Gly or Absent and R1 is
      NH2 or OH
<220> FEATURE:
<223> OTHER INFORMATION: Description of Artificial Sequence: synthetic
      peptide

<400> SEQUENCE: 13

Ala Glu Gly Thr Phe Thr Ser Asp Val Ser Ser Tyr Leu Glu Gly Gln
 1               5                  10                  15

Ala Ala Lys Glu Phe Ile Ala Trp Leu Val Xaa Gly Arg Xaa
            20                  25                  30

<210> SEQ ID NO 14
<211> LENGTH: 31
<212> TYPE: PRT
<213> ORGANISM: Artificial Sequence
<220> FEATURE:
<221> NAME/KEY: VARIANT
<222> LOCATION: 28
<223> OTHER INFORMATION: Xaa = Lys or Arg
<220> FEATURE:
<221> NAME/KEY: VARIANT
<222> LOCATION: 31
<223> OTHER INFORMATION: Xaa = X1-R1 where X1 is Gly or Absent and R1 is
      NH2 or OH
<220> FEATURE:
<223> OTHER INFORMATION: Description of Artificial sequence: synthetic
      peptide

<400> SEQUENCE: 14

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Xaa Gly Arg Xaa
            20                  25                  30

<210> SEQ ID NO 15
<211> LENGTH: 31
<212> TYPE: PRT
<213> ORGANISM: Artificial sequence
<220> FEATURE:
<221> NAME/KEY: VARIANT
<222> LOCATION: 2
<223> OTHER INFORMATION: Xaa = D-Ala
<220> FEATURE:
<221> NAME/KEY: VARIANT
```

```
<222> LOCATION: 28
<223> OTHER INFORMATION: Xaa = Lys or Arg
<220> FEATURE:
<221> NAME/KEY: VARIANT
<222> LOCATION: 31
<223> OTHER INFORMATION: Xaa = X1-R1 where X1 is Gly or Absent and R1 is
      NH2 or OH
<220> FEATURE:
<223> OTHER INFORMATION: Description of Artificial sequence: synthetic
      peptide

<400> SEQUENCE: 15

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Arg Xaa
            20                  25                  30

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial sequence
<220> FEATURE:
<223> OTHER INFORMATION: Description of Artificial Sequence: synthetic
      peptide

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 18
<211> LENGTH: 31
<212> TYPE: PRT
<213> ORGANISM: Artificial sequence
<220> FEATURE:
<223> OTHER INFORMATION: Description of Artificial Sequence: synthetic
      peptide

<400> SEQUENCE: 18

His Gly Glu Gly Thr Phe Thr Ser Asp Leu Ser Lys Gln Met Glu Glu
1               5                   10                  15

Ala Val Arg Leu Phe Ile Glu Trp Leu Lys Asn Gly Gly Pro Tyr
            20                  25                  30

<210> SEQ ID NO 19
<211> LENGTH: 31
<212> TYPE: PRT
```

```
<213> ORGANISM: Artificial Sequence
<220> FEATURE:
<223> OTHER INFORMATION: Description of Artificial Sequence: synthetic
      peptide

<400> SEQUENCE: 19

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Tyr
            20                  25                  30

<210> SEQ ID NO 20
<211> LENGTH: 31
<212> TYPE: PRT
<213> ORGANISM: Artificial sequence
<220> FEATURE:
<223> OTHER INFORMATION: Description of Artificial Sequence: synthetic
      peptide

<400> SEQUENCE: 20

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
            20                  25                  30

<210> SEQ ID NO 21
<211> LENGTH: 37
<212> TYPE: PRT
<213> ORGANISM: Artificial Sequence
<220> FEATURE:
<223> OTHER INFORMATION: Description of Artificial sequence: synthetic
      peptide

<400> SEQUENCE: 21

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Lys
        35

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Lys
            20                  25                  30

<210> SEQ ID NO 23
<211> LENGTH: 40
<212> TYPE: PRT
<213> ORGANISM: Artificial Sequence
<220> FEATURE:
<223> OTHER INFORMATION: Description of Artificial sequence: synthetic
      peptide

<400> SEQUENCE: 23

His Gly Glu Gly Thr Phe Thr Ser Asp Leu Ser Lys Gln Met Glu Glu
 1               5                  10                  15
```

```
Glu Ala Val Arg Leu Phe Ile Glu Trp Leu Lys Asn Gly Gly Pro Ser
            20                  25                  30

Ser Gly Ala Pro Pro Ser Lys
            35                  40

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys
            35                  40

<210> SEQ ID NO 25
<211> LENGTH: 31
<212> TYPE: PRT
<213> ORGANISM: Artificial Sequence
<220> FEATURE:
<223> OTHER INFORMATION: Description of Artificial sequence: synthetic
      peptide

<400> SEQUENCE: 25

His Gly Glu Gly Thr Phe Thr Ser Asp Leu Ser Lys Glu Met Glu Glu
 1               5                  10                  15

Glu Val Arg Leu Phe Ile Glu Trp Leu Lys Asn Gly Gly Pro Tyr
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial sequence: synthetic
      peptide

<400> SEQUENCE: 26

His Gly Glu Gly Thr Phe Thr Ser Asp Leu Ser Lys Glu Met Glu Glu
 1               5                  10                  15

Glu Val Arg Leu Phe Ile Glu Trp Leu Lys Asn Gly Gly Tyr
            20                  25                  30

<210> SEQ ID NO 27
<211> LENGTH: 29
<212> TYPE: PRT
<213> ORGANISM: Artificial sequence
<220> FEATURE:
<223> OTHER INFORMATION: Description of Artificial Sequence: synthetic
      peptide

<400> SEQUENCE: 27

Asp Leu Ser Lys Gln Met Glu Glu Glu Ala Val Arg Leu Phe Ile Glu
 1               5                  10                  15

Trp Leu Lys Gly Gly Pro Ser Ser Gly Pro Pro Pro Ser
            20                  25

<210> SEQ ID NO 28
```

```
<211> LENGTH: 40
<212> TYPE: PRT
<213> ORGANISM: Artificial Sequence
<220> FEATURE:
<221> NAME/KEY: BINDING
<222> LOCATION: 40
<223> OTHER INFORMATION: Xaa represents Lys (E-AEEA-MPA)-NH2 linked to
      Albumin Cysteine 34 thiol and where "E" represents Epsilon
<220> FEATURE:
<223> OTHER INFORMATION: Description of Artificial sequence: Synthetic
      Peptide

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 29
<211> LENGTH: 40
<212> TYPE: PRT
<213> ORGANISM: Artificial Sequence
<220> FEATURE:
<221> NAME/KEY: BINDING
<222> LOCATION: 40
<223> OTHER INFORMATION: Xaa represents Lys (E-AEEA-MPA)-NH2 linked to
      S, O or NH of a protein and where "E" represents Epsilon
<220> FEATURE:
<223> OTHER INFORMATION: Description of Artificial Sequence: Synthetic
      Peptide

<400> SEQUENCE: 29

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 30
<211> LENGTH: 31
<212> TYPE: PRT
<213> ORGANISM: Artificial Sequence
<220> FEATURE:
<221> NAME/KEY: VARIANT
<222> LOCATION: 2
<223> OTHER INFORMATION: Xaa = D-Ala
<220> FEATURE:
<221> NAME/KEY: BINDING
<222> LOCATION: 31
<223> OTHER INFORMATION: Xaa represents Lys (E-AEEA-MPA)-NH2 linked to
      S, O or NH of a protein and where "E" represents Epsilon
<220> FEATURE:
<223> OTHER INFORMATION: Description of Artificial Sequence: Synthetic
      Peptide

<400> SEQUENCE: 30

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
            20                  25                  30
```